United States Patent [19]

Bruderlein et al.

[11] 4,054,569
[45] Oct. 18, 1977

[54] BENZOCYCLOHEPTAISOQUINOLINE DERIVATIVES

[75] Inventors: Francois T. Bruderlein, Montreal; Leslie G. Humber, Dollard des Ormeaux, both of Canada

[73] Assignee: Ayerst McKenna & Harrison Ltd., Montreal, Canada

[21] Appl. No.: 686,971

[22] Filed: May 17, 1976

Related U.S. Application Data

[60] Division of Ser. No. 518,853, Oct. 29, 1974, Pat. No. 3,985,751, which is a continuation-in-part of Ser. No. 242,839, April 10, 1972, Pat. No. 3,852,452, which is a continuation-in-part of Ser. No. 97,481, Dec. 20, 1970, Pat. No. 3,914,305, which is a continuation-in-part of Ser. No. 10,306, Feb. 10, 1970, Pat. No. 3,657,250.

[51] Int. Cl.$^2$ .......................................... C07D 217/04

[52] U.S. Cl. ...................... 260/287 P; 260/288 CE; 260/289 C

[58] Field of Search .......... 260/289 C, 287 P, 288 CE

[56] References Cited

U.S. PATENT DOCUMENTS 3,361,751  1/1968  Humber et al. ................. 260/289 C

*Primary Examiner*—Paul M. Coughlan, Jr.
*Attorney, Agent, or Firm*—Adley F. Mandel

[57] ABSTRACT

Octahydrobenzo[6,7]-(or [5,6]-)cyclohepta-[1,2,3-de]-pyrido-(or pyrrolo-)[2,1-a]isoquinolines, and decahydrobenzo[6,7]-(or[5,6]-)cyclohepta[1,2,3-de]-azepino[2,1-a]isoquinolines and derivatives thereof, optionally substituted on the pyrrolidine, piperidine or azepine ring. The compounds are useful CNS depressants, anticonvulsant and antiinflammatory agents, and methods for their preparation and use are also disclosed.

66 Claims, No Drawings

BENZOCYCLOHEPTAISOQUINOLINE DERIVATIVES

This is a division of application Ser. No. 518,853, filed Oct. 29, 1974, now U.S. Pat. No. 3,985,751 which is a Continuation-in-Part of our earlier-filed U.S. Pat. application Ser. No. 242,839, filed Apr. 10, 1972, now U.S. Pat. No. 3,852,452, which is a Continuation-Part of application Ser. No. 97,481, filed Dec. 20, 1970, now U.S. Pat. No. 3,914,305 which in turn is a Continuation-in-Part of U.S. Patent application Ser. No. 10,306, filed Feb. 10, 1970, issued as U.S. Pat. No. 3,657,250 on Apr. 18, 1972.

BACKGROUND OF THE INVENTION

The present invention relates to benzocycloheptaisoquinoline derivatives, to intermediates used in their preparation, and to processes for preparing these compounds.

The benzocycloheptaisoquinoline derivatives of this invention possess valuable pharmacologic properties. For example, the compounds exhibit useful central nervous system depressant, anticonvulsant and antiinflammatory properties. Especially noteworthy are the central nervous system depressant properties of the compounds. More specifically, the benzocycloheptaisoquinoline derivatives of this invention have a more favourable separation of useful central nervous system depressant effects from ataxic properties and undesirable autonomic nervous system effects that are possessed by most other such depressants. In addition, the benzocycloheptaisoquinoline derivatives possess a low order of toxicity.

The combination of attributes stated above renders the benzocycloheptaisoquinolines of this invention useful and desirable as therapeutic agents.

SUMMARY OF THE INVENTION

The benzocycloheptaisoquinoline derivatives of this invention are represented by formula I or formula Ia,

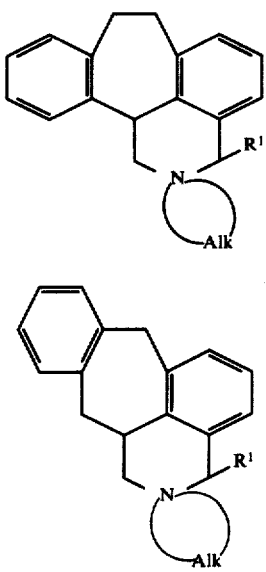

in which $R^1$ represents a hydrogen or a lower alkyl and Alk represents the organic radicals

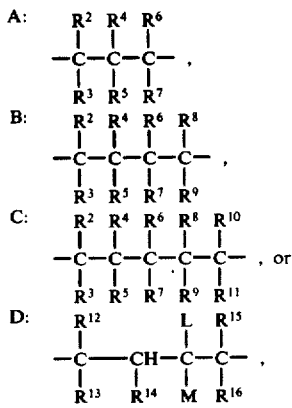

designated A,B,C or D, respectively, in which $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are the same or different selected from the group consisting of hydrogen and lower alkyl with the proviso that the carbon atom to which $R^2$ and $R^3$ or $R^{12}$ and $R^{13}$ are attached is bonded to the nitrogen atom of formula I, L represents a hydroxyl or a lower alkanoyloxy; and M is hydrogen, lower alkyl, lower alkenyl, lower alkynyl, a cycloalkyl containing 3 – 6 carbon atoms which may be optionally substituted with a lower alkyl, phenyl or phenyl substituted with lower alkyl, lower alkoxy, halo, or trihalomethyl; benzyl, furyl, thienyl, or pyridyl.

DETAILS OF THE INVENTION

This benzocycloheptaisoquinoline derivatives of this invention are capable of forming acid addition salts with pharmaceutically acceptable acids. Such acid addition salts are included within the scope of this invention.

The acid addition salts are prepared by reacting the base form of the benzocycloheptaisoquinoline derivative with either one equivalent or preferably an excess of the appropriate acid in an organic solvent, such as ether or an ethanol-ether mixture. Such salts may advantageously be used for the purpose of isolating and/or purifying the compounds of this invention, and may be transformed in a manner known per se into the corresponding salts with pharmaceutically acceptable acids. These salts, when administered to mammals, possess the same pharmacologic activities as the corresponding bases. For many purposes it is preferable to administer the salts rather than the base compounds. Among the acid addition salts suitable for this purpose are salts such as the sulfate, phosphate, lactate, tartrate, maleate, citrate and hydrochloride. Both the base compounds and the above acid addition salts have the distinct advantage of possessing a relatively low order of toxicity.

Also included in this invention are the stereo-chemical isomers of the compounds of formula I and Ia which result from asymmetric centers, contained therein. These isomeric forms may be prepared by different methods and are purified readily by crystallization or chromatography.

Individual optical isomers, which might be separated by fractional crystallization of the diastereoisomeric salts formed thereof, for instance, with d- or l- tartaric acid or D-(+)-α-bromocamphor sulfonic acid, are also included.

The preferred compounds of formula 1 are those in which $R^1$ is hydrogen and Alk is the organic radical of formula D in which L is hydroxyl or lower alkanoyloxy and M is lower alkyl, lower alkenyl, lower alkynyl, a cycloalkyl containing 3 - 6 carbon atoms which may be optionally substituted with lower alkyl, phenyl or phenyl substituted with lower alkyl, lower alkoxy, halo, or trihalomethyl; benzyl, furyl, thienyl, or pyridyl, in which the hydroxyl or lower alkanoyloxy group is trans to the hydrogen atom in position 15b. The wavy line attaching the hydrogen atom in position 6B indicates that it may be either cis or trans to the hydrogen atom in position 15b. Those compounds may be represented by the following formula 1b

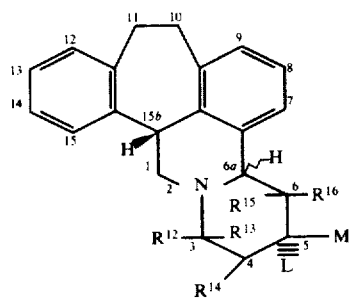

1b

The useful central nervous system depressent activity and the anticonvulsant activity of the benzocycloheptaisoquinoline derivatives of formulae I and Ia and their acid addition salts with pharmaceutically acceptable acids may be demonstrated in standard pharmacologic tests, such as, for example, the tests described by R. A. Turner in "Screening Methods in Pharmacology", Academic Press, New York and London, 1965, pp. 60 - 99 and 164 - 172, respectively.

Preferred compounds with central nervous system depressant activity include, 1,4,5,6,6a,10,11,15b-octahydro-3H-benzo[6,7]cyclohepta[1,2,3-de]pyrido[2,1-a]isoquinoline, 5-t-butyl-1,4,5,6,6a,10,11,15b-octahydro-3H-benzo[6,7]cyclohepta[1,2,3-de]pyrido[2,1-a]isoquinolin-5-ol, 5-isopropyl-1,4,5,6,6a,10,11,15b-octahydro-3H-benzo[6,7]cyclohepta[1,2,3-de]-pyrido[2,1-a]isoquinolin-5-ol, and 5-t-butyl-1,4,5,6,6a,10,15,15a-octahydro-3H-benzo[5,6]cyclohepta[1,2,3-de]pyrido[2,1-a]isoquinolin-5-ol, and particularly the A isomers thereof (see below for an explanation of the term, isomer A).

When the benzocycloheptaisoquinoline derivatives of this invention are used as central nervous system depressants for treating psychoses, neuroses or depression or as anticonvulsant agents in mammals, e.g. rats and mice, they may be used alone or in combination with pharmacologically acceptable carriers, the proportion of which is determined by the solubility and chemical nature of the compound, chosen route of administration and standard biological practice. For example, they may be administered orally in solid form containing such excipients as starch, milk sugar, certain types of clay and so forth. They may also be administered orally in the form of solutions or they may be injected parenterally. For example, enough saline or glucose to make the solution isotonic.

The dosage of the present therapeutic agents will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered for central nervous system depressant and/or anti-convulsant purposes at a concentration level that will generally afford effective results without causing any harmful or deleterious side effects and preferably at a level that is in a range of from about 0.5 mg to about 500 mg per kilo per day, although as aforementioned variations will occur. However, a dosage level that is in the range of from about 5 mg to about 100 mg per kilo per day is most desirably employed in order to achieve effective results.

The benzocycloheptaisoquinoline derivatives of this invention possess another useful pharmacologic property; that is, they are useful an antiinflammatory agents. More particularly, the said compounds of this invention exhibit antiinflammatory activity in standard pharmacologic tests, for example, the tests similar to those described by Robert A. Turner in "Screening Methods in Pharmacology", Academic Press, pp.152-163,1965, based on the reduction of pedal inflammation.

When the benzocycloheptaisoquinoline derivatives of this invention are employed as antiinflammatory agents in mammals, e.g. in rats, they may be administered orally, alone or in tablets combined with pharmacologically acceptable excipients, such as starch, milk sugar and so forth. They may also be administered orally in the form of solutions in suitable vehicles such as vegetable oils.

The dosage of the benzocycloheptaisoquinoline derivatives of this invention will vary with the particular compound chosen and form of administration. Furthermore, it will vary with the particular host under treatment. Generally, the compounds of this invention are administered for antiinflammatory purposes at a concentration level that affords protective effects without any deleterious side effects. These effective concentration levels are usually obtained within a therapeutic range of 10 mg to 100 mg per kilo per day, with a preferred range of 25 mg to 50 mg per kilo per day.

For the preparation of the benzocycloheptaisoiquinolines of formula I, in which Alk represents organic radical A, B or C, we have found it convenient to use the process illustrated by FIG. 1 in which $R^1$ is as defined above, Alk is organic radical A, B or C, Y represents the hydroxyl group or chlorine, bromine or iodine and X represents the nucleophilic residue derived from a condensing agent used in the Bischler-Napieralski reaction such as a bromine or chlorine or a phosphate.

FIG. 1
(Alk = organic radical A, B or C)

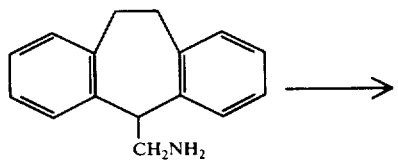

II.

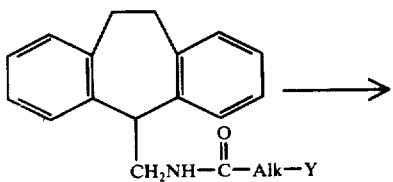

III.

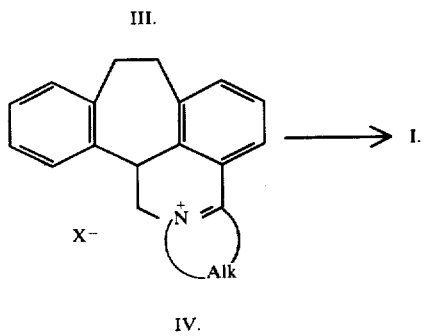

IV.

In practising the above process, 10,11-dihydro-5H-dibenzo[a,d]cycloheptene-5-methylamine (II), described by L. G. Humber et al., J. Heterocyclic Chem., 3, 247 (1966), is condensed with an appropriate lactone of general formula

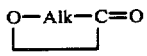

in which Alk is organic radical A, B or C, as defined above, to yield the corresponding hydroxyamide of formula III in which Y is the hydroxyl group. The appropriate lactones utilized in this condensation are either available commercially, for example, butyrolactone, δ-valerolactone, or α-methyl-γ-butyrolactone, or they are described with a variety of methods for their preparation in organic chemistry textbooks, such as the textbook, "Methoden der Organischen Chemie", Houben-Weyl, E. Muller, Ed., Vol. VI/2, Georg Thieme Verlag, Stuttgart, 1963, pp. 561–852.

Convenient conditions for this condensation include heating the dibenzocycloheptenemethylamine of formula II and the appropriate lactone together at a temperature from 100 in 180° C for a period ranging from two to 24 hours.

Although the condensation may be accomplished without the use of solvent, the use of an inert solvent, such as an aromatic hydrocarbon, for example, benzene, or a lower alkanol, for example ethanol, is preferred. When this condensation is performed in a solvent, then it is preferable to conduct the reaction at the boiling point of the reaction mixture for a period of seven to 24 hours.

The corresponding hydroxyamide of formula III in which Y is the hydroxyl group, thus obtained, is subjected to the conditions of the Bischler-Napieralski reaction, see for example, W. M. Whaley and T. R. Govindachari in Organic Reactions, 6, 74 (1951). Subsequent heating of the crude product from this reaction in an inert solvent, preferably benzene, promotes the completion of the conversion to the quaternary salt of formula IV in which Alk is organic radical A, B or C and X is defined as above. Preferred reaction conditions for the Bischler-Napieralski reaction include the use of phosphorus oxychloride as the condensing agent, temperatures ranging from 50 to 150° C, a reaction time of one to four hours and the use of toluene or benzene as solvent.

Reduction of the quaternary salt of formula IV, obtained as described above, with either an alkali metal borohydride, in inert solvents such as, for instance, methanol or water, or by means of catalytically activated hydrogen, using preferably Raney nickel or palladium or platinum catalyst, in solvents such as, for example, ethanol, acetic acid or tetrahydrofuran, affords one isomer of the compounds of formula I in which Alk is organic radical A, B or C and R¹ represents a hydrogen atom. For convenience, this isomer is designated as isomer B and is one of the configurational isomers, discussed above.

On the other hand reduction of the quaternary salts of formula IV in the presence of a metal, for example, zinc, with an acid, for example, hydrochloric acid, using an appropriate solvent such as ethanol, affords another isomer of the compounds of formula I in which Alk is organic radical A, B or C and R¹ represents a hydrogen atom. For convenience, this isomer is designated as isomer A.

Hence, this present designation of A and B isomers to compounds in this application is used to distinguish between those stereochemical isomers having different asymmetric centers at the junction of the two rings having the nitrogen atom in common.

Furthermore, it is possible to convert either of the isomers A or B or formula I, in which Alk is organic radical A, B or C and R¹ represents a hydrogen atom, into the other. This interconversion is effected by oxidizing either of the above isomers A and B with mercuric acetate or lead tetraacetate, preferably the former, followed by treatment with an appropriate acid of formula HX in which X is as defined above, to regenerate the corresponding quaternary salt of formula IV described above. Subsequent reduction of said quaternary salt, according to a method, described above, for affording the isomer different from the one originally oxidized, completes the interconversion.

We would add that the definition of X, and in turn the definition of the acid, HX, used in the above description of the interconversion of one isomer to the other, may be broadened to include any nucleophilic residue derived from an acid, for example, perchloric acid or lactic acid, capable of forming a quaternary salt of the class represented by formula IV. Such quaternary salts, such as, for example, quaternary salts of formula IV in which X represents a perchlorate or lactate, are then reduced in the aforementioned manner to give the desired other isomer.

In a variation of the process described above, II→• III→IV→I, the starting material of formula II is condensed with an appropriate ω-haloalkanoic acid halide of formula Z-Alk-COZ¹ in which Alk is organic radical A, B or C and Z and Z¹ are the same or different and each represent chlorine, bromine or iodine to yield the corresponding haloamide of formula III in which Y is a chlorine, bromine or iodine. This condensation is achieved according to the same conditions employed above for the conversion of the starting material of formula II to the hydroxyamide of formula III in which Y is the hydroxyl group except that an excess, preferably a three to five molar excess, of a neutralizing agent for instance, sodium carbonate, is employed to combine with the acid formed as a by-product during the reaction.

The haloamide of formula III thus obtained is then subjected to the conditions of the Bischler-Napieralski reaction, described above, to afford the quaternary salt of formula IV which is reduced to compounds of formula I in which $R^1$ is hydrogen and Alk is organic radical A, B or C according to methods described above.

The appropriate ω-haloalkanoic acid halides used in the preceding process are prepared from their corresponding acids by treatment with thionyl chloride, thionyl bromide or phosphorus triiodide. The corresponding ω-haloalkanoic acids are either commercially available or are described with a variety of methods for their preparation in organic chemistry textbooks, for instance, see description by M. F. Ansell and R. H. Gigg in "Rodd's Chemistry of Carbon Compounds", Vol. I, part C, S. Coffey, Ed., 2nd. Ed., Elsevier Publishing Co., Amsterdam, 1965, pp. 201-214.

Alternatively, the above ω-haloalkanoic acid halides in which Z and $Z^1$, are the same may be readily prepared by treating the lactones of general formula

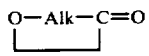

in which Alk is organic radical A, B or C with thionyl chloride, thionyl bromide or phosphorus triiodide according to the methods such as described in "Methoden der Organischen Chemie", Houben-Weyl, E. Muller, Ed., Vol. VI/2, Georg Thieme Verlag, Stuttgart, 1963, pp. 561-852.

Also, the practise of the present process and its variation (see FIGS. 1, II→III→IV→I) includes the preparation of the benzocycloheptaisoquinolines of formula I in which Alk is organic radical A, B or C and $R^1$ represents a lower alkyl. The latter compounds are obtained by the action of a lower alkyl magnesium halide on the corresponding quaternary salt of formula IV according to the conditions generally used for the Grignard reaction. For a description of these conditions, see L. Fieser and M. Fieser, "Advanced Organic Chemistry", Reinhold Publishing Corp., New York, 1961, p. 270. Preferred conditions for this reaction include a temperature range from room temperature to the boiling point of the mixture, a reaction time from 30 minutes to four hours and the use of ether or tetrahydrofuran as solvent.

Alternatively, the quaternary salt of formula IV in which Alk is organic radical A, B or C may be prepared by an entirely different process. In this case the starting material is 10,11-dihydro-5H-dibenzo[a,d]cycloheptane-5-carboxaldehyde (V) which is readily obtained by the action of the Grignard reagent prepared from chloromethyl methyl ether and magnesium, on 10,11-dihydro-5H-dibenzo[a,d]cyclohepten-5-one, described by S. O. Winthrop et al., J. Org. Chem., 27, 230 (1962). Reductive alkylation of 10,11-dihydro-5H-dibenzo[a,d]cycloheptene-5-carboxaldehyde with an appropriate aminoester of general formula $NH_2$—Alk—$COOR^{17}$ in which Alk is organic radical A, B or C and $R^{17}$ is a lower alkyl, according to the methods described by A. R. Surrey and H. F. Hammer, J. Am. Chem. Soc., 66, 2127 (1944) or A. Skita and W. Stichmer, German Pat. No. 716,668 (Chem. Abstr., 38, 2345, 1944) for the preparation of derivatives of p-aminobenzoic acid, yields the cyclic amide VI. Treatment of the latter compound according to the conditions of the Bischler-Napieralski reaction, described above, affords the desired quaternary salt of formula IV in which Alk and X are as described above.

The appropriate aminoesters used in the preceding process are prepared by the usual esterification procedures, of their corresponding free acids, see for example, L. Fieser and M. Fieser, cited above, pp. 370-380. The corresponding free acids are either available commercially, for example, 4-aminobutyric acid, 5-aminovaleric acid or 6-aminocaproic acid or are described with a variety of methods for their preparation in organic chemistry textbooks, such as the textbook, "Methoden der Organischen Chemie", Houben-Weyl, E. Muller, Ed., Vol. XI/2, Georg Thieme Verlag, Stuttgart, 1958, pp. 269-509.

Accordingly, the alternate preparation of the quaternary salt of formula IV, in which Alk and X are as defined above, from another starting material constitutes an alternative process for the preparation of the benzocycloheptaisoquinolines of formula I, which may be represented schematically by FIG. 2 in which $R^1$, Alk and X are as defined above.

FIG. 2 (Alk = organic radial A, B or C)

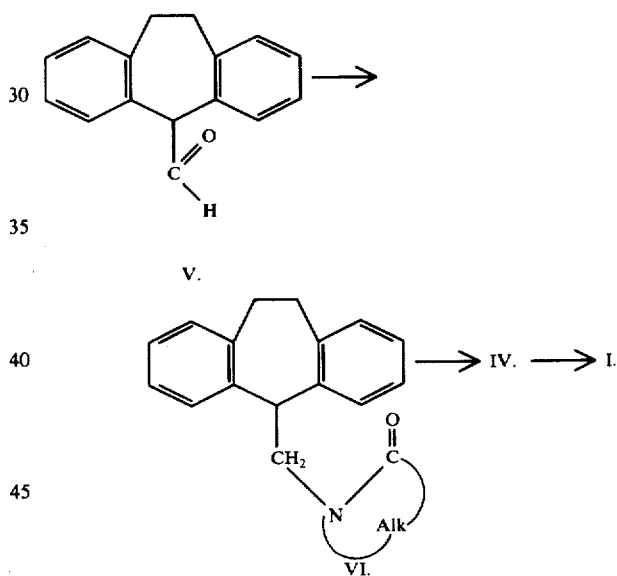

The benzocycloheptaisoquinoline derivatives of formula I of this invention in which $R^1$ is hydrogen or lower alkyl and Alk is organic radical D may be prepared by the process illustrated by FIG. 3 in which $R^2$, $R^3$, $R^4$, $R^5$, $R^9$, $R^{12}$, $R^{13}$, $R^{14}$, $R^{15}$ and $R^{16}$ are as defined in the first instance.

Fig. 3

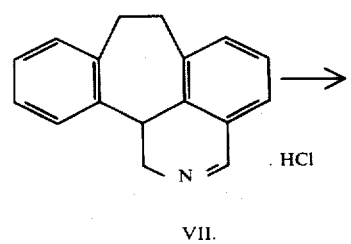

-continued

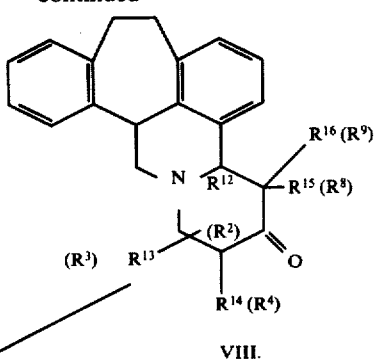

I (R¹ = H or lower alkyl and Alk = organic radial D)

This process is based in part on the synthesis of 1,2,3,4,6,6a,10,11,15b-octahydro-5H-benzo[6,7]cyclohepta[1,2,3de]pyrido[2,1-a]isoquinolin-5-one (VIII, $R^{12}$, $R^{13}$, $R^{14}$, $R^{15}$ and $R^{16}$ = H) described previously by L. G. Humber et al., Can. J. Chem. 46, 2981 (1968) and by L. G. Humber and M. A. Davis, U.S. Patent No. 3,361,751, issued Jan. 2, 1968.

In practising the process represented by FIG. 3, an acid addition salt, preferably the hydrochloric acid addition salt, of 1,7,8,12b-tetrahydrobenzo[1,2]cyclohepta[3,4,5-de]isoquinoline (VII), described by L. G. Humber et al., J. Heterocyclic Chem., 3, 247 (1966), is allowed to react with an unsaturated ketone of the formula $R^2R^3C=CR^4COCHR^8R^9$ or $R^{12}R^{13}C=CR^{14}COCHR^{15}R^{16}$ in which $R^2$, $R^3$, $R^4$, $R^8$, $R^9$, $R^{12}$, $R^{13}$, $R^{14}$, $R^{15}$ and $R^{16}$ are as defined in the first instance, to yield the aminoketone of formula VIII in which $R^2$, $R^3$, $R^4$, $R^8$, $R^9$, $R^{12}$, $R^{13}$, $R^{14}$, $R^{15}$ and $R^{16}$ are as defined in the first instance. This extremely facile reaction may be performed in an inert solvent, for example dimethylformamide, dimethylsulfoxide, dioxane, or lower alkanois, preferably ethanol; however, when using the lower-molecular weight unsaturated ketones, for example methyl vinyl ketone or ethyl vinyl ketone, it is equally convenient to employ an excess of the unsaturated ketone as solvent for the reaction. Generally, this reaction is performed by heating the components together with or without an inert solvent. Preferred conditions for this reaction include heating the mixture on a steam bath for prolonged periods of time, for example, from 30 minutes to four hours.

Most of the unsaturated ketones used in the preceding reaction are available commercially; the remainder are described or may be prepared by general methods cited in organic chemistry textbooks and publications, see for example, "Rodd's Chemistry of the Carbon Compounds", Vol. I, part C, S. Coffey, Ed., 2nd ed., Elsevier Publishing Co., Amsterdam, 1965, pp. 81–91 or D. Beke and C. Szántay, Chem. Ber., 95, 2132 (1962).

If desired, the aminoketone of formula VIII may be separated into the A and B isomers by chromatography and purified by recrystallization.

The aminoketone of general formula VIII may be converted to the benzocycloheptaisoquinoline derivatives of formula I in which R¹ is hydrogen or lower alkyl and Alk is organic radical D by several methods. Among the preferred methods is the procedure whereby the aminoketone is allowed to react with a lower alkyl, lower alkylene, lower alkynyl, cycloalkyl, containing 3-6 carbon atoms which may be optionally substituted with a lower alkyl, or phenyl magnesium halide according to the conditions of the Grignard reaction, cited above. In this manner, there are obtained the compounds of formula I in which R¹ is hydrogen and Alk is organic radical D wherein $R^{12}$, $R^{13}$, $R^{14}$ and $R^{15}$ and $R^{16}$ are as defined in the first instance, L is a hydroxyl and M is other than hydrogen as defined in the first instance (in those compounds where M represents a cycloalkyl containing 3 - 6 carbon atoms which is optionally substituted with a lower alkyl, said lower alkyl substituent is preferably located at the position 1 of the cycloalkyl. The latter compounds may be readily converted to their corresponding derivatives of formula I in which R¹ is a lower alkyl by oxidizing said latter compounds with mercuric acetate or lead tetraacetate, followed by acid treatment according to the first two steps of the procedure described above for converting either of the isomers A or B of formula I into each other, and treating the resulting, corresponding quaternary salt of formula IV with a lower alkyl magnesium halide according to the conditions of the Grignard reaction, cited above.

Alternatively, the aminoketone of formula VIII may be reacted with appropriate lower alkyl lithium derivatives; cycloalkyl lithium derivatives, containing 3-6 carbons, which may be optionally substituted with a lower alkyl; vinyl lithium; allyl lithium; methallyl lithium; lithium acetylide; 1-propynyl lithium; 2-propynyl lithium, or phenyl lithium; in an inert solvent by essentially the same technique employed in the Grignard reaction. In this manner, the said aminoketones are converted to compounds of formula I in which R¹ is hydrogen and Alk is organic radical D in which $R^{12}$, $R^{13}$, $R^{14}$, $R^{15}$, and $R^{16}$ are as defined in the first instance, L is a hydroxyl and M is lower alkyl, cycloalkyl containing 3-6 carbon atoms which may be optionally substituted with a lower alkyl; vinyl, allyl, methallyl, ethynyl, 1-propynyl, 2-propynyl or phenyl, respectively.

It should be noted that the present conversion of aminoketones of formula VIII to the above compounds of formula I may be effected by the addition of other organoalkali metal reagents. For example, sodium or potassium acetylide may replace lithium acetylide. However, this use of other organoalkali metal reagents is most suitable for preparing compounds of formula I in which Alk is organic radical D in which M is a lower 1-alkynyl.

Furthermore, the compounds of formula I in which Alk is organic radical D in which M is lower alkenyl or alkynyl are readily reduced with hydrogen in the presence of a catalyst to their corresponding lower alkyl derivatives.

Alternatively, the aminoketone of formula VIII may be treated with a reducing agent, e.g. an alkali metal borohydride or lithium aluminum hydride, to yield the corresponding compound of formula I in which Alk is organic radical D, wherein L is hydroxyl and M is hydrogen, viz., the 5-alcohol described below.

The esterified derivatives of the compounds of formula I in which R¹ is hydrogen or lower alkyl and Alk is organic radical D wherein L is a lower alkeneyloxy are otained by treating the corresponding compounds in which L is a hydroxyl, prepared as described above, with the appropriate acid anhydride, at temperatures ranging from 0°-120° C, from 6 - 48 hours, in the presence of sodium acetate.

In another aspect of this invention the aminoketone of general formula VIII may be used conveniently to prepare those benzocycloheptaisoquinolines of this invention of formula I in which R¹ is hydrogen and Alk is organic radical B in which R², R³, R⁴, R⁸ and R⁹ are as defined in the first instance, R⁵ and R⁷ are hydrogen and R⁶ is either a hydrogen or a lower alkyl. In other words, the carbonyl of the aminoketone of general formula VIII may either be reduced to a methylene, or a lower alkyl group may be introduced at the carbonyl site of the aminoketone.

In the first case, where the carbonyl of the aminoketone is reduced to a methylene group, several methods may be employed. These methods include both one step reduction, such as the Clemmensen reduction or the Wolff-Kishner reduction, or reduction through a reducible intermediate such as, for instance, the corresponding derivative of the aminoketone of formula VIII having a thioketal or tosyloxy group in place of the cabonyl group. Said derivative having the tosyloxy group is obtained by reduction of the corresponding aminoketone of formula VIII, preferably with sodium borohydride or lithium aluminum hydride, followed by tosylation of the resulting corresponding 5-alcohol of formula I in which R¹ is hydrogen, and Alk is organic radical D wherein R¹² - R¹⁶ are as defined in the first instance, L is hydroxyl, and M is hydrogen. Said last-named 5-alcohol is obtained in two isomeric forms. For a general description of these methods refer to O.H. Wheeler in "The Chemistry of the Carbonyl Group", S. Patai, Ed., Interscience Publishers, London, 1966, pp. 507-566. In practice we have found that an especially convenient manner for reducing the carbonyl group to the methylene group is to convert the aminoketone of formula VIII to its corresponding thioketal derivative with ethanedithiol and an acid catalyst, for example, boron trifluoride etherate. The resulting thioketal derivative is then reduced with Raney nickel to the desired benzocycloheptaisoquinoline derivative of this invention of formula I in which R¹ is hydrogen and Alk is organic radical B in which R², R³, R⁴, R⁸, and R⁹ are hydrogen or lower alkyl and R⁵, R⁶ and R⁷ are hydrogen.

In the second case where a lowerr alkyl is introduced at the carbonyl site of the aminoketone of general formula VIII, the aminoketone is allowed to react with a lower alkyl magnesium halide or lower alkyl lithium derivative as described above, followed by dehydration of the resulting tertiary carbinol with an acid catalyst, for example, p-toluenesulfonic acid, and then catalytic hydrogenation, using the conditions described above, to yield the desired benzocycloheptaisoquinoline of formula I.

Alternatively, the alkyl group may be introduced at the site of the carbonyl group of the aminoketone of formula VIII, by reacting the aminoketone with a lower alkylidenephosphorane according to the conditions of the Wittig reaction; see A. Maercker, Organic Reactions, 14, 270 (1965), followed by catalytic reduction of the resulting alkylidene derivative.

Thus in this second case, there are obtained the benzocycloheptaisoquinolines of the invention of formula I in which R¹ is hydrogen and Alk is organic radical B in which R², R³, R⁴, R⁶, R⁸ and R⁹ are hydrogen or lower alkyl and R⁵ and R⁷ are hydrogen.

For the preparation of the benzocycloheptaisoquinolines of formula Ia in which Alk represents organic radicals, A, B, or C, the processes disclosed herein for the preparation of corresponding benzocycloheptaisoquinolines of formula I are used with the provision that the tricyclic starting materials for these processes are chosen with regard to the structural variation required to lead to the desired compounds of formula Ia. Accordingly, in applying one such process, described above dependent on the compound of formula II as starting material, then the appropriate choice for replacing the starting material of formula II is 10,11-dihydro-5H-dibenzo-[a,d]cycloheptene-10-methylamine (IIa) in order to prepare the corresponding desired benzocycloheptaisoquinoline of formula Ia.

In other words the process II→III→IV→I and its variations, described herein for the preparation of the benzocycloheptaisoquinolines of formula I in which Alk represents organic radical A, B or C, are utilized with starting material IIa whereby the preparation of the corresponding benzocyclohepta-isoquinolines of formula Ia is achieved in the manner illustrated by FIG. 4 in which R¹, X and Y are as defined hereinbefore and Alk is organic radical A, B or C.

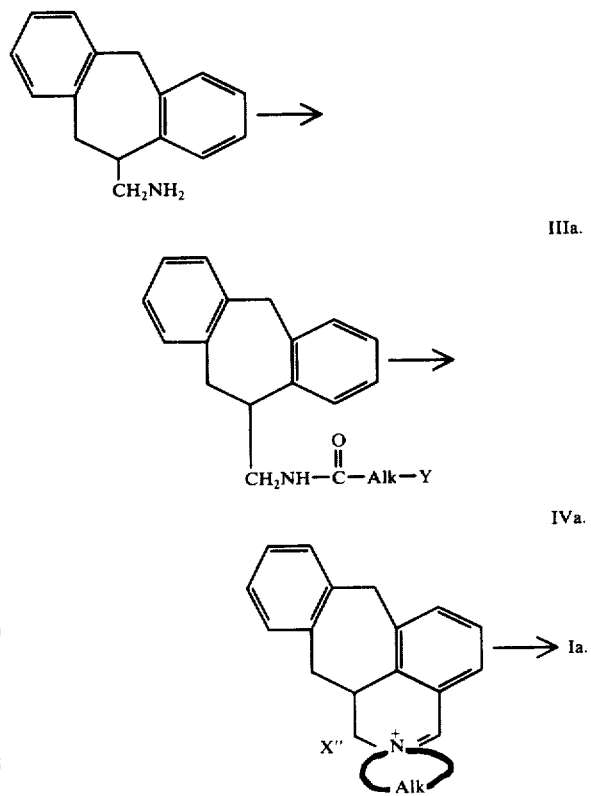

Fig. 4
(Alk = organic radical A, B or C)

Likewise, in applying the process, described above, dependent on the compound of formula V as starting material, the corresponding desired benzocycloheptaisoquinoline of formula Ia is obtained by appropriately choosing 10,11-dihydro-5H-dibenzo-[a,d]cycloheptene-10-carboxaldehyde (Va) to replace the compound of formula V. In this case the process is represented by FIG. 5 in which R¹ and X are as defined hereinbefore and Alk is organic radical A, B or C.

Fig. 5
(Alk = organic radical A, B or C)

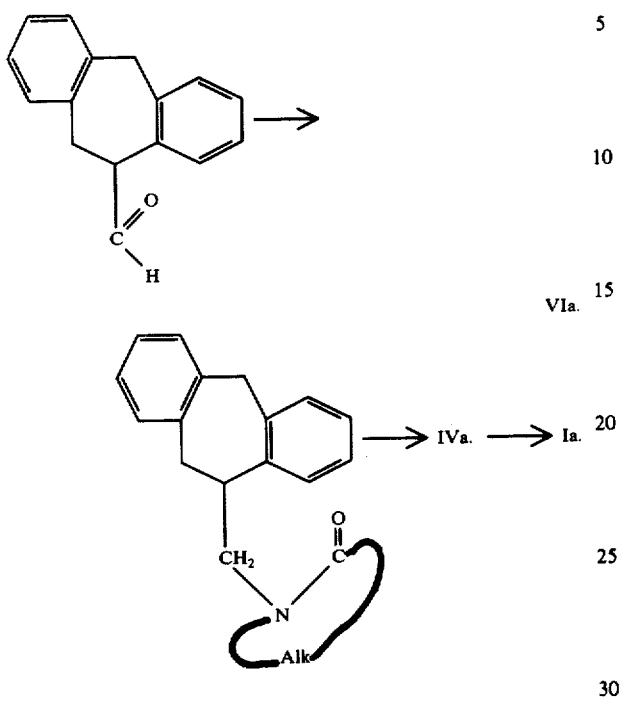

FIG. 6

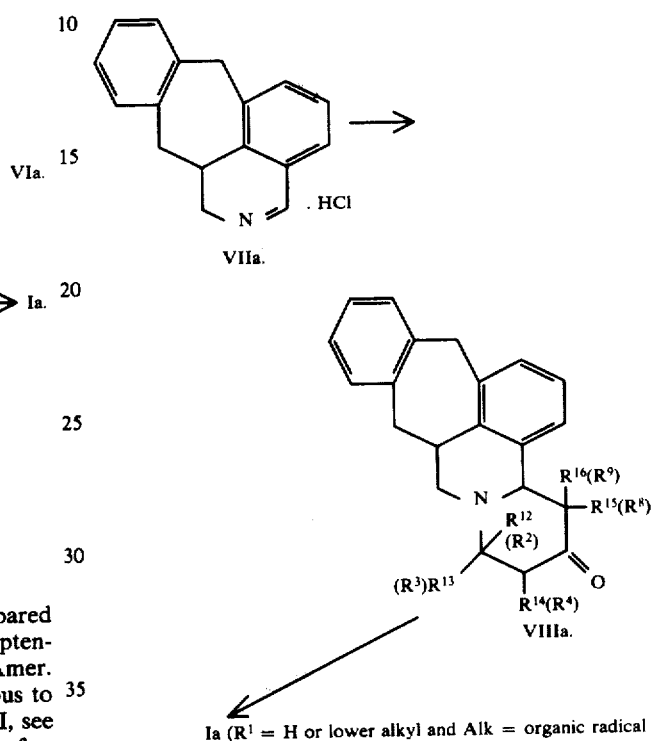

Ia (R¹ = H or lower alkyl and Alk = organic radical D)

The starting material of formula IIa may be prepared from 10,11-dihydro-5H-dibenzo[a,d]cyclohepten-10-one, described by N.J. Leonard et al., J. Amer. Chem. Soc., 77, 5078 (1955), by methods analogous to those used to prepare the compound of formula II, see Humber, et al., (1966 and 1968), cited above, and references therein, from its corresponding dibenzocyclohepten-5-one. A preparation of this starting material which we have found convenient is the following:

10,11-Dihydro-5H-debenzo[a,d]cyclohepten-10-one is treated with triethyl phosphonoacetate in the presence of sodium hydride in tetrahydrofuran according to the conditions of the Wittig reaction, see Maercker, cited above, to afford 10,11-dihydro-5H-dibenzo[a,d]-cycloheptene-$\Delta^{10,\alpha}$-acetic acid methyl ester. The latter product is hydrolyzed with potassium hydroxide in aqueous methanol to give the corresponding acid. The acid is hydrogenated in the presence of 10% palladium on carbon in ethanol at room temperature and 1000 psi to give 10,11-dihydro-5H-dibenzo[a,d]cycloheptene-10-acetic acid. Subsequent conversion of this latter acid to the starting material of formula IIz is achieved readily according to the procedure described by S. H. Alam and D.B. MacLean, Can. J. Chem., 43, 3433 (1965) for converting 9-xantheneacetic acid to 9-xanthenemethylamine.

The starting material of formula Va, utilized above, is prepared readily from 10,11-dihydro-5H-dibenzo[a,d]-cyclo-hepten-10-one according to the procedure disclosed herein for converting 10,11-dihydro-5H-dibenzo[a,d]cyclohepten-5-one to the compound of formula V.

The benzocycloheptaisoquinolines of formula Ia in which Alk is organic radical D are prepared by the processes described herein for the preparation of their corresponding analogs of formula I with the provision that instead of compound VII, the requisite starting material is an acid addition salt, preferably the hydrochloric acid addition salt, of 1,7,12,12a-tetrahydrobenze[1,2]cyclohepta[4,5,6-de]isoquinoline (VIIa). In this case the process is represented by FIG. 6, in which R², R³, R⁴, R⁸, R⁹, R¹², R¹³, R¹⁴, R¹⁵ and R¹⁶ are as defined in the first instance.

Compound VIIa is prepared from the compound of formula IIa, described above, according to the procedure described by Number et al., (1966), cited above, for converting 10,11-dihydro-5H-dibenzo[a,d]cycloheptene-5-methylamine (II) to the hydrochloric acid addition salt of 1,7,8,12b-tetra-hydrobenzo[1,2]cyclohepta[3,4,5-de]isoquinoline (VII).

Finally, and if desired, the intermediate aminoketone VIIIa, obtained in the processes for the preparation of the compounds of formula Ia in which Alk is organic radical D, is converted to the corresponding benzocycloheptaisoquinolines of formula Ia in which R¹ is hydrogen and Alk is organic radical B in which R², R³, R⁴ R⁸ and R⁹ are as defined in the first instance, R⁵ and R are hydrogen and R⁶ is either hydrogen or lower alky by the procedure described herein for the similar conversion the aminoketone of formula VIII to the corresponding benzocyclo-heptaisoquinolines of formula I.

The term "lower alkyl" as used herein contemplate: straight chain alkyl radicals containing from one to si: carbon atoms and branched chain alkyl radical contain ing up to four carbon atoms and includes methyl, ethyl propyl, isopropyl, butyl, isobutyl, and the like.

The term "lower alkenyl" as used herein contem plates both straight and branched alkenyl radicals con taining from two to six carbon atoms and includes vinyl allyl, 1-propenyl, methallyl, 2-ethyl-3-butenyl and th like.

The term "lower alkynyl" as used herein contem plates both straight and branched alkynyl radicals con aining from two to six carbon atoms and includes ethynyl, 2-propenyl, 3-methyl-1-butynyl and the like.

The term "lower cycloalkyl" as used herein contemplates saturated cyclic hydrocarbon radicals containing from three to six carbon atoms and includes cyclopropyl, cyclobutyl, cyclopentyl and cyclohexyl.

The term "lower alkanoyloxy" as used herein contemplates both straight chain alkanoyloxy radicals containing from two to ten carbon atoms and branched chain alkanoyloxy radicals containing from four to six carbon atoms and includes acetoxy, propionyloxy, pivaloyloxy, hexanoyloxy and the like.

The term "halo" as used herein contemplates halogens and includes fluorine, chlorine, bromine and iodine.

The following Examples will illustrate further this invention.

EXAMPLE 1

10,11-Dihydro-5H-dibenzo[a,d]cycloheptene-5-methyl-amine (8.5 g) and Y-butyrolactone (3.7 g) are heated at 150° C. (internal temperature) for one hour. After cooling, the solid residue is recrystallized from benzene to give N-[(10,11-dihydro-5H-dibenzo[a,d]cyclohepten-5-yl)methyl]-4-hydroxy-butyramide, (III, Alk = $CH_2CH_2CH_2$ and Y = OH), m.p. 103°–105° C.

In the same manner, but using an equivalent amount of

α-methyl-, β-methyl- or γ-methyl-γ-butyrolactone,
α-ethyl-, β-ethyl- or γ-ethyl-γ-butyrolactone,
α-propyl-, β-propyl- or γ-propyl-γ-butyrolactone,
α,α-dimethyl-, β,β-dimethyl- or γ,γ-dimethyl-γ-butyrolactone,
αα-diethyl-, ββ-diethyl- or γ,γ-diethyl-γ-butyrolactone,
α,α-dipropyl-, β,β-dipropyl-or γ,γ-dipropyl-γ-butyrolactone,
α,β-dimethyl-, α,γ-dimethyl- or β,γ-dimethyl-γ-butyrolactone,
α-methyl-β-ethyl-, α-ethyl-β-propyl- or β-propyl-γ-methyl-γ-butyrolactone,
α,β,γ-trimethyl-, α-methyl-β-ethyl-γ-propyl-,
α,α,β,γ-tetramethyl-, α,α-dimethyl-β-ethyl-γ-propyl,
α,αγ-trimethyl-β,β-diethyl- or α,α,β,β,γ-pentamethyl-γ-propyl-γ-butyrolactone, or δ-valerolactone,
α-methyl-, β-methyl-, γ-methyl- or δ-methyl-δ-valerolactone,
α-ethyl-, β-ethyl-, γ-ethyl-, or δ-ethyl-δ-valerolactone,
α-propyl-, β-propyl-, γ-propyl- or δ-propyl-δ-valerolactone,
α,α-dimethyl-, β,β-dimethyl-, γ,γ-dimethyl- or δ,δ-dimethyl-δ-valerolactone,
α,α-diethyl-, β,β-diethyl-, γ,γ-diethyl- or δ,δ-diethyl-δ-valerolactone,
α,β-dimethyl-, α,γ-dimethyl-, α,δ-dimethyl- or β,γ-dimethyl- δ-valerolactone,
α,β-diethyl- α,γ-diethyl-α,δ-dipropyl or β,γ-dipropyl-δ-valerolactone,
α-ethyl-β-methyl-, or α-propyl-δ-methyl-δ-valerolactone,
α,β, γ-trimethyl- or α,β-dimethyl-γ-propyl -δ-valerolactone,
α, β,γ,δ-tetramethyl-, α, β,γ,δ-tetraethyl-δ-methyl-, α, α, β, β, γ, γ-hexamethyl-, α, α,β, β, γ, γ, δ-heptamethyl- or
α, α,β, β, γ, γ,δ, δ-octamethyl-δ-valerolactone, ε-caprolactone, α-methyl-, β-methyl-, γ-methyl-,δ-methyl- or ε-methyl-ε-caprolactone,
α, α-dimethyl-, αγ-diethyl-α-propyl-ε-methyl-,α,γ,δ,ε-tetraethyl-, α-propyl-β,ε,ε-triethyl-γ-methyl-, α,α,β,βγ, γ-hexamethyl- or α,α,β,β, γ,γ,ε-heptamethyl-ε-ethyl-ε-caprolactone instead of δ-butyrolactone,
N-[(10,11-dihydro-5H-dibenzo[a,d]cyclohepten-5-yl)methyl]-4-hydroxy-2-methylbutyramide,-4-hydroxy-3-methylbutyramide, -4-hydroxy-valeramide, m.p. 112°–113° C.,
-4-hydroxy-2-ethylbutyramide, -4-hydroxy-3-ethylbutyramide,
4-hydroxy-caproamide, -4-hydroxy-2-propylbutyramide,
-4-hydroxy-3-propylbutyramide, -4-hydroxy-heptanamide,
-4-hydroxy-2,2-dimethylbutyramide,
-4-hydroxy-3,3-dimethylbutyramide,
-4-hydroxy-4-methylvaleramide,
-4-hydroxy-2,2-diethylbutyramide,
-4-hydroxy-3,3-diethylbutyramide,
-4-hydroxy-4-ethylcaproamide,
-4-hydroxy-2,2-dipropylbutyramide,
-4-hydroxy-3,3-dipropylbutyramide,
-4-hydroxy-4-propylheptanamide,
-4-hydroxy-2,3-dimethylbutyramide,
-4-hydroxy-2,4-dimethylbutyramide,
-4-hydroxy-3-methylvaleramide,
-4-hydroxy-2-methyl-3-ethylbutyramide,
-4-hydroxy-2-ethyl-3-propylbutyramide,
-4-hydroxy-2-propylvaleramide,
-4-hydroxy-2,3-dimethylvaleramide,
-4-hydroxy-2-methyl-3-ethylheptanamide,
-4-hydroxy-2,2,3-trimethylvaleramide,
-4-hydroxy-2,2-dimethyl-3-ethylheptanamide,
-4-hydroxy-2,2-dimethyl-3,3-diethylvaleramide,
-4-hydroxy-2,2,3,3,4-pentamethylheptanamide, -5-hydroxy-valeramide, m.p. 102° C., -5-hydroxy-2-methylvaleramide,
5-hydroxy-3-methylvaleramide, -5-hydroxy-5-methylvaleramide,
-5-hydroxycaproamide,
-5-hydroxy-2-ethylvaleramide, -5-hydroxy-3-ethylvaleramide,
-5-hydroxy-4-ethylvaleramide, -5-hydroxy-heptanamide,
-5-hydroxy-2-propylvaleramide,
5-hydroxy-3-propylvaleramide, -5-hydroxy-4-propylvaleramide, -5-hydroxyoctanamide,
-5-hydroxy-2,2-dimethylvaleramide,
-5-hydroxy-3,3-dimethylvaleramide,
-5-hydroxy-4,4-dimethylvaleramide, -5-hydroxy-5-methylcaproamide,
-5-hydroxy-2,2-diethylvaleramide,
-5-hydroxy-3,3-diethylvaleramide,
-5- hydroxy-4,4- diethylvaleramide,
-5-hydroxy-5-ethylheptanamide,
-5-hydroxy-2,3-dimethylvaleramide,
-5-hydroxy-2,4-dimethylvaleramide,
-5-hydroxy-2-methylcaproamide,
-5-hydroxy-3,4-dimethylvaleramide,
-5-hydroxy-2,3-diethylvaleramide,
-5-hydroxy-2,4-diethylvaleramide,
-5-hydroxy-2-propyloctanamide,
-5-hydroxy-3,4-dipropylvaleramide,
-5-hydroxy-2-ethyl-3-methylvaleramide,
-5-hydroxy-2-propylcaproamide, -5-hydroxy-2,3,4-trimethylvaleramide,
-5-hydroxy-2,3-dimethyloctanamide,
-5-hydroxy-2,3,4-trimethylcaproamide,
-5-hydroxy-2,3-diethyl-4,4-diethylcaproamide,
-5-hydroxy-2,2,3,3,4,4-hexamethylvaleramide,
-5-hydroxy-2,2,3,3,4,4-hexamethylcaproamide,
-5-hydroxy-2,2,3,3,4,4,5-heptamethylcaproamide,
-6-hydroxycaproamide,
-6-hydroxy-2-methylcaproamide,
-6-hydroxy-3-methylcaproamide,
-6-hydroxy-4-methylcaproamide,
-6-hydroxy-5-methylcaproamide,
-6-hydroxy-heptanamide,
-6-hydroxy-2,2-dimethylcaproamide,
-6-hydroxy-2,4-diethyl-2-propylheptanamide,
-6-hydroxy-2,4,5-triethyloctanamide,
-6-hydroxy-2-propyl-3,5-diethyl-4-methyloctanamide,
-6-hydroxy-2,2,3,3,4,4-hexamethylcaproamide and
-6-hydroxy-2,2,3,3,4,4,5-heptamethyloctanamide, are obtained.

EXAMPLE 2

To a solution of N-[(10,11-dihydro-5H-dibenzo[a,d]-cyclohepten-5-yl)methyl]-5-hydroxyvaleramide (24.0 g), prepared as described in Example 1, in 400 ml. of toluene is added phosphorus oxychloride (150 ml) and the reaction mixture is refluxed for three hours. After cooling, dilution with petroleum ether precipitates an oil. The supernatant layer is decanted and the residual oil is dissolved in benzene. The benzene solution is washed with water, 10% sodium hydroxide solution and then water again, dried and subjected to reflux for 40 minutes to complete the quaternary salt formation. The resulting precipitate is recrystallized from acetone to give 1,3,4,5,6,10,11,15b-octahydrobenzo[6,7]cyclohepta[1,2,3,-de]-pyrido[2,1-a]isoquinolinium chloride (IV, Alk = $CH_2CH_2CH_2CH_2$ and X = Cl), m.p. 205°–207° C.

The procedure of Example 2 may be followed to make other quaternary salts of formula IV. Examples of such quaternary salts are listed in Tables I, II and III. In each of these cases an equivalent amount of the starting material listed is used instead of N-[10,11-dihydro-5H-dibenzo[a,d]-cyclohepten-5-yl)methyl]-5-hydroxyvaleramide used in Example 2. The particular starting materials listed below are described in Example 1.

TABLE I

| EXAMPLE | STARTING MATERIAL (FORMULA III IN WHICH Y = OH AND Alk IS STRUCTURE LISTED BELOW) | PRODUCT [(PREFIX LISTED BELOW)-1,4,5,9,10,14b-HEXAHYDRO-3H-BENZO[6,7]CYCLOHEPTA-[1,2,3-de]PYRROLO[2,1-a]-ISOQUINOLINIUM CHLORIDE] |
|---|---|---|
| 3 | $CH_2CH_2CH_2$ | parent quaternary salt, 1,4,5,9,10,14b-hexahydro-3H-benzo[6,7]cyclohepta[1,2,3-de]-pyrrolo[2,1-a]isoquinolinium chloride, m.p. 209° C. |
| 4 | $CH(CH_3)CH_2CH_2$ | 5-methyl- |
| 5 | $CH_2CH(CH_3)CH_2$ | 4-methyl- |
| 6 | $CH_2CH_2CH(CH_3)$ | 3-methyl- |
| 7 | $CH(C_2H_5)CH_2CH_2$ | 5-ethyl- |
| 8 | $CH_2CH(C_2H_5)CH_2$ | 4-ethyl- |
| 9 | $CH_2CH_2CH_2(C_2H_5)$ | 3-ethyl- |
| 10 | $CH(C_3H_7)CH_2CH_2$ | 5-propyl- |
| 11 | $CH_2CH(C_3H_7)CH_2$ | 4-propyl- |
| 12 | $CH_2CH_2CH(C_3H_7)$ | 3-propyl- |
| 13 | $C(CH_3)_2CH_2CH_2$ | 5,5-dimethyl- |
| 14 | $CH_2C(CH_3)_2CH_2$ | 4,4-dimethyl- |
| 15 | $CH_2CH_2C(CH_3)_2$ | 3,3-dimethyl- |
| 16 | $C(C_2H_5)_2CH_2CH_2$ | 5,5-diethyl- |
| 17 | $CH_2C(C_2H_5)_2CH_2$ | 4,4-diethyl- |
| 18 | $CH_2CH_2C(C_2H_5)_2$ | 3,3-diethyl- |
| 19 | $C(C_3H_7)_2CH_2CH_2$ | 5,5-dipropyl- |
| 20 | $CH_2C(C_3H_7)_2CH_2$ | 4,4-dipropyl- |
| 21 | $CH_2CH_2C(C_3H_7)_2$ | 3,3-dipropyl- |
| 22 | $CH(CH_3)CH(CH_3)CH_2$ | 5,4-dimethyl- |
| 23 | $CH(CH_3)CH_2CH(CH_3)$ | 5,3-dimethyl- |
| 24 | $CH_2CH(CH_3)CH(CH_3)$ | 4,3-dimethyl- |
| 25 | $CH(CH_3)CH(C_2H_5)CH_2$ | 5-methyl-4-ethyl- |
| 26 | $CH(C_2H_5)CH(C_3H_7)CH_2$ | 5-ethyl-4-propyl- |
| 27 | $CH_2CH(C_3H_7)CH(CH_3)$ | 4-propyl-3-methyl- |
| 28 | $CH(CH_3)CH(CH_3)CH(CH_3)$ | 5,4,3-trimethyl- |
| 29 | $CH(CH_3)CH(C_2H_5)CH(C_3H_7)$ | 5-methyl-4-ethyl-3-propyl- |
| 30 | $C(CH_3)_2CH(CH_3)CH(CH_3)$ | 5,5,4,3-tetramethyl- |
| 31 | $C(CH_3)_2CH(C_2H_5)CH(C_3H_7)$ | 5,5-dimethyl-4-ethyl-3-propyl- |
| 32 | $C(CH_3)_2C(C_2H_5)_2CH(CH_3)$ | 5,5,3-trimethyl-4,4-diethyl- |
| 33 | $C(CH_3)_2C(CH_3)_2C(CH_3)(C_2H_5)$ | 5,5,4,4,3-pentamethyl-3-propyl- |

TABLE II

| EXAMPLE | STARTING MATERIAL (FORMULA III IN WHICH Y = OH AND Alk IS STRUCTURE LISTED BELOW) | PRODUCT [(PREFIX LISTED BELOW)-1,3,4,5,6,10,11,15b-OCTAHYDRO-BENZO[6,7]-CYCLOHEPT-[1,2,3-de]-PYRIDO[2,1-a ISOQUINOLINIUM CHLORIDE] |
|---|---|---|
| 34 | $CH(CH_3)CH_2CH_2CH_2$ | 6-methyl- |
| 35 | $CH_2CH(CH_3)CH_2CH_2$ | 5-methyl- |
| 36 | $CH_2CH_2CH(CH_3)CH_2$ | 4-methyl- |
| 37 | $CH_2CH_2CH_2CH(CH_3)$ | 3-methyl- |
| 38 | $CH(C_2H_5)CH_2CH_2CH_2$ | 6-ethyl- |

TABLE II-continued

| EXAMPLE | STARTING MATERIAL (FORMULA III IN WHICH Y = OH AND Alk IS STRUCTURE LISTED BELOW) | PRODUCT [(PREFIX LISTED BELOW)-1,3,4,5,6,10,11,15b-OCTAHYDRO-BENZO[6,7]-CYCLOHEPT-[1,2,3-de]-PYRIDO[2,1-a ISOQUINOLINIUM CHLORIDE] |
|---|---|---|
| 39 | $CH_2CH(C_2H_5)CH_2CH_2$ | 5-ethyl- |
| 40 | $CH_2CH_2CH(C_2H_5)CH_2$ | 4-ethyl- |
| 41 | $CH_2CH_2CH_2CH(C_2H_5)$ | 3-ethyl- |
| 42 | $CH(C_3H_7)CH_2CH_2CH_2$ | 6-propyl- |
| 43 | $CH_2CH(C_3H_7)CH_2CH_2$ | 5-propyl- |
| 44 | $CH_2CH_2CH(C_3H_7)CH_2$ | 4-propyl- |
| 45 | $CH_2CH_2CH_2CH(C_3H_7)$ | 3-propyl- |
| 46 | $C(CH_3)_2CH_2CH_2CH_2$ | 6,6-dimethyl- |
| 47 | $CH_2C(CH_3)_2CH_2CH_2$ | 5,5-dimethyl- |
| 48 | $CH_2CH_2C(CH_3)_2CH_2$ | 4,4-dimethyl- |
| 49 | $CH_2CH_2CH_2C(CH_3)_2$ | 3,3-dimethyl- |
| 50 | $C(C_2H_5)_2CH_2CH_2CH_2$ | 6,6-diethyl- |
| 51 | $CH_2C(C_2H_5)_2CH_2CH_2$ | 5,5-diethyl- |
| 52 | $CH_2CH_2C(C_2H_5)_2CH_2$ | 4,4-diethyl- |
| 53 | $CH_2CH_2CH_2C(C_2H_5)_2$ | 3,3-diethyl- |
| 54 | $CH(CH_3)CH(CH_3)CH_2CH_2$ | 6,5-dimethyl- |
| 55 | $CH(CH_3)CH_2CH(CH_3)CH_2$ | 6,4-dimethyl- |
| 56 | $CH(CH_3)CH_2CH_2CH(CH_3)$ | 6,3-dimethyl- |
| 57 | $CH_2CH(CH_3)CH_2CH(CH_3)$ | 5,3-dimethyl- |
| 58 | $CH(C_2H_5)CH(C_2H_5)CH_2CH_2$ | 6,5-diethyl- |
| 59 | $CH(C_2H_5)CH_2CH(C_2H_5)CH_2$ | 6,4-diethyl- |
| 60 | $CH(C_3H_7)CH_2CH_2CH(C_3H_7)$ | 6,3-dipropyl- |
| 61 | $CH_2CH(C_3H_7)CH_2CH(C_3H_7)$ | 5,3-dipropyl- |
| 62 | $CH(C_2H_5)CH(CH_3)CH_2CH_2$ | 6-ethyl-5-methyl- |
| 63 | $CH(C_3H_7)CH_2CH_2CH(CH_3)$ | 6-propyl-3-methyl- |
| 64 | $CH(CH_3)CH(CH_3)CH(CH_3)CH_2$ | 6,5,4-trimethyl- |
| 65 | $CH(CH_3)CH(CH_3)CH_2CH(C_3H_7)$ | 6,5-dimethyl-3-propyl- |
| 66 | $CH(CH_3)CH(CH_3)CH(CH_3)CH(CH_3)$ | 6,5,4,3-tetramethyl- |
| 67 | $CH(C_2H_5)CH(C_2H_5)C(C_2H_5)_2$-CH(CHhd 3) | 6,5,4,4-tetraethyl-3-methyl- |
| 68 | $C(CH_3)_2C(CH_3)_2C(CH_3)_2CH_2$ | 6,6,5,5,4,4-hexamethyl- |
| 69 | $C(CH_3)_2C(CH_3)_2C(CH_3)_2CHCH_3$ | 6,6,5,5,4,4,3-heptamethyl- |
| 70 | $C(CH_3)_2C(CH_3)_2C(CH_3)_2C(CH_3)_2$ | 6,6,5,5,4,4,3,3-octamethyl- |

TABLE III

| EXAMPLE | STARTING MATERIAL (FORMULA III IN WHICH Y = OH AND Alk IS STRUCTURE LISTED BELOW) | PRODUCT [(PREFIX LISTED BELOW)-1,3,4,5,6,7,11,12,16b-OCTAHYDRO-3H-BENZO[6,7]CYCLOHEPTA[1,2,3-de]-AZEPINO[2,1-a]ISOQUINOLINIUM CHLORIDE] |
|---|---|---|
| 71 | $CH_2CH_2CH_2CH_2CH_2$ | parent quaternary salt, 1,4,5,6,7,11,12,16b-octahydro-3H-benzo[6,7]cyclohepta-[1,2,3-de]azepino[2,1-a]isoquinolinium chloride |
| 72 | $CH(CH_3)CH_2CH_2CH_2CH_2$ | 7-methyl- |
| 73 | $CH_2CH(CH_3)CH_2CH_2CH_2$ | 6-methyl- |
| 74 | $CH_2CH_2CH(CH_3)CH_2CH_2$ | 5-methyl- |
| 75 | $CH_2CH_2CH_2CH(CH_3)CH_2$ | 4-methyl- |
| 76 | $CH_2CH_2CH_2CH_2CH(CH_3)$ | 3-methyl- |
| 77 | $C(CH_3)_2CH_2CH_2CH_2CH_2$ | 7,7-dimethyl- |
| 78 | $C(C_2H_5)(C_3H_7)CH_2CH(C_2H_5)$-$CH_2CH(CH_3)$ | 7,5-diethyl-7-propyl-3-methyl- |
| 79 | $CH(C_2H_5)CH_2CH(C_2H_5)CH$-$(C_2H_5)CH(C_2H_5)$ | 7,5,4,3-tetraethyl- |
| 80 | $CH(C_3H_7)CH(C_2H_5)CH(CH_3)$-$CH_2C(C_2H_5)_2$ | 7-propyl-6,3,3-triethyl-5-methyl- |
| 81 | $C(CH_3)_2C(CH_3)_2C(CH_3)_2$-$CH_2CH_2$ | 7,7,6,6,5,5-hexamethyl- |
| 82 | $C(CH_3)_2C(CH_3)_2C(CH_3)_2$-$CH_2C(CH_3)(C_2H_5)$ | 7,7,6,6,5,5,3-heptamethyl-3-ethyl- |

EXAMPLE 83

To a solution of the quaternary salt, 1,4,5,9,10,14b-hexahydro-3H-benzo[6,7]cyclohepta[1,2,3-de]pyrrolo[2,1-a]-isoquinolinium chloride (4.0 g), described in Example 3, in 100 ml of methanol, sodium borohydride (4.0 g) is added portionwise. The reaction mixture is refluxed for one hour. After removal of the solvent the residue is taken up in water and extracted with ether. The ether extract is dried and evaporated to dryness. The residue is crystallized from hexane to yield 1,3,4,5,5a,9,10,14b-octahydrobenzo[6,7]-cyclohepta[1,2,3-de]pyrrolo[2,1-a]isoquinoline (Isomer B) (I, $R^1$ = H and Alk = $CH_2CH_2CH_2$), m.p. 112°-113° C. The corresponding hydrochloric acid addition salt of this free base has m.p. 253°-254° C. (recrystallized from acetone).

The above isomer B of Example 83 as well as the corresponding Isomer A, may also be prepared by following the procedure of Example 85, see below, by using an equivalent amount of quaternary salt noted in Example 83 instead of the quaternary salt noted in Example 85. Accordingly, 1,3,4,5,5a,9,10,14b-octahydrobenzo[6,7]-cyclohepta[1,2,3-de]-pyrrolo[2,1-a]isoquinoline (Isomer A), m.p. 76°-77° C, is obtained. The corresponding hydrochloric acid addition salt of the latter compound has m.p. 226° C.

EXAMPLE 84

The quaternary salt, 1,3,4,5,6,10,11,15b-octahydrobenzo[6,7]cyclohepta[1,2,3-de]pyrido[2,1-a]isoquinolinium chloride (1.3 g), described in Example 2, is dissolved in 50 ml. of ethanol and subjected to hydrogenation at room temperature under atmospheric pressure in the presence of platinum oxide (50 mg). After a reaction time of two hours, the catalyst is removed by filtration and the filtrate is evaporated to dryness. The residue is crystallized from hexane to afford 1,4,5,6,6a,10,11,15b-octahydro-3H-benzo- [6,7]cyclohepta[1,2,3-de]pyrido[2,1-a]isoquinoline (Isomer B) (I, $R^1$ = H and Al = $CH_2CH_2CH_2CH_2$), m.p. 136° C. The corresponding hydrochloric acid addition salt of this free base has m.p. 235°–236° C.

EXAMPLE 85

A mixture of the quaternary salt, 1,3,4,5,6,10,11,15b-octahydrobenzo[6,7]cyclohepta[1,2,3-de]pyrido[2,1-a]isoquinolinium chloride (2.0 g) and zinc dust (4.0 g) in 40 ml of concentrated hydrochloric acid and 150 ml of ethanol is heated on a steam bath for one hour. The alcohol is removed by evaporation and the remainder of the mixture is rendered neutral with concentrated ammonia. The mixture is then extracted with benzene. The benzene extract is dried and evaporated to dryness. The residue is subjected to chromatography on 120 g of neutral alumina (activity II). Elution with hexane affords 1,4,5,6,6a 10,11,15b-octahydro-3H-benzo[6,7]cyclohepta[1,2,3-de]- pyrido[2,1-a]isoquinoline (Isomer B), identical with the product described in Example 84. Subsequent elution with benzene affords the corresponding Isomer A. Recrystallization of this Isomer A from hexane affords crystals, m.p. 90°–92° C.

The hydrochloride addition salt of 1,4,5,6,6a 10,11,15b- octahydro-3H-benzo[6,7]cyclohepta[1,2,3-de]pyrido[2,1-a]isoquinoline (Isomer A) has m.p. 255°–260° C., after recrystallization from acetone.

The procedures of Examples 83, 84 and 85 and the procedure of Example 85 may be followed to prepare the B or A isomers, respectively, of the compounds of formula I noted in those Examples or other benzocycloheptaisoquinoline derivatives of formula I in which $R^1$ is a hydrogen. In each case an equivalent amount of appropriate starting material, a quaternary salt of formula IV to give the desired product is used in place of the quaternary salts noted in Examples 83, 84 and 85. Examples of such benzocycloheptaisoquinoline derivatives which may be prepared by these procedures are listed in Tables IV, V and VI with a notation referring to the source of the appropriate starting material.

TABLE IV

| EXAMPLE | NUMBER OF EXAMPLE DESCRIBING QUATERNARY SALT STARTING MATERIAL | PRODUCT [(PREFIX LISTED BELOW)-1,3,4,5,5a,9,10,14b-OCTAHYDRO-BENZO[6,7]CYCLOHEPTA[1,2,3-de]-PYRROLO[2,1-a]ISOQUINOLININE] |
|---|---|---|
| 86 | 4 | 5-methyl- |
| 87 | 5 | 4-methyl- |
| 88 | 6 | 3-methyl-[Isomer B has the following characteristics in its nmr spectrum (CDCl₃): δ7.8 (H), 7.4–6.65(6H), 4.49 (H), 3.3–1.6 (12 H), 1.38 (CH₃)] |
| 89 | 7 | 5-ethyl- |
| 90 | 8 | 4-ethyl- |
| 91 | 9 | 3-ethyl- |
| 92 | 10 | 5-propyl- |
| 93 | 11 | 4-propyl- |
| 94 | 12 | 3-propyl- |
| 95 | 13 | 5,5-dimethyl- |
| 96 | 14 | 4,4-dimethyl- |
| 97 | 15 | 3,3-dimethyl- |
| 98 | 16 | 5,5-diethyl- |
| 99 | 17 | 4,4-diethyl- |
| 100 | 18 | 3,3-diethyl- |
| 101 | 19 | 5,5-dipropyl- |
| 102 | 20 | 4,4-dipropyl- |
| 103 | 21 | 3,3-dipropyl- |
| 104 | 22 | 5,4-dimethyl- |
| 105 | 23 | 5,3-dimethyl- |
| 106 | 24 | 4,3-dimethyl- |
| 107 | 25 | 5-methyl-4-ethyl- |
| 108 | 26 | 5-ethyl-4-propyl- |
| 109 | 27 | 4-propyl-3-methyl- |
| 110 | 28 | 5,4,3-trimethyl- |
| 111 | 29 | 5-methyl-4-ethyl-3-propyl- |
| 112 | 30 | 5,5,4,3-tetramethyl- |
| 113 | 31 | 5,5-dimethyl-4-ethyl-3-propyl- |
| 114 | 32 | 5,5,3-trimethyl-4,4-diethyl- |
| 115 | 33 | 5,5,4,4,3-pentamethyl-3-propyl- |

TABLE V

| EXAMPLE | NUMBER OF EXAMPLE DESCRIBING QUATERNARY SALT STARTING MATERIAL | PRODUCT [(PREFIX LISTED BELOW)-1,4,5,6,6a,10,11,15b-OCTAHYDRO-3H-BENZO[6,7]CYCLOHEPTA[1,2,3-de]-PYRIDO[2,1-a]ISOQUINOLINE] |
|---|---|---|
| 116 | 34 | 6-methyl- |
| 117 | 35 | 5-methyl- |
| 118 | 36 | 4-methyl- |
| 119 | 37 | 3-methyl- |
| 120 | 38 | 6-ethyl- |
| 121 | 39 | 5-ethyl- |
| 122 | 40 | 4-ethyl- |
| 123 | 41 | 3-ethyl- |

TABLE V-continued

| EXAMPLE | NUMBER OF EXAMPLE DESCRIBING QUATERNARY SALT STARTING MATERIAL | PRODUCT [(PREFIX LISTED BELOW)-1,4,5,6,6a,10,11,15b-OCTAHYDRO-3H-BENZO[6,7]CYCLOHEPTA[1,2,3-de]-PYRIDO[2,1-a]ISOQUINOLINE] |
|---|---|---|
| 124 | 42 | 6-propyl- |
| 125 | 43 | 5-propyl- |
| 126 | 44 | 4-propyl- |
| 127 | 45 | 3-propyl- |
| 128 | 46 | 6,6-dimethyl- |
| 129 | 47 | 5,5-dimethyl- |
| 130 | 48 | 4,4-dimethyl- |
| 131 | 49 | 3,3-dimethyl- |
| 132 | 50 | 6,6-diethyl- |
| 133 | 51 | 5,5-diethyl- |
| 134 | 52 | 4,4-diethyl- |
| 135 | 53 | 3,3-diethyl- |
| 136 | 54 | 6,5-dimethyl- |
| 137 | 55 | 6,4-dimethyl- |
| 138 | 56 | 6,3-dimethyl- |
| 139 | 57 | 5,3-dimethyl- |
| 140 | 58 | 6,5-diethyl- |
| 141 | 59 | 6,4-diethyl- |
| 142 | 60 | 6,3-dipropyl- |
| 143 | 61 | 6,3-dipropyl- |
| 144 | 62 | 6-ethyl-5-methyl- |
| 145 | 63 | 6-propyl-3-methyl- |
| 146 | 64 | 6,5,4-trimethyl- |
| 147 | 65 | 6,5-dimethyl-3-propyl- |
| 148 | 66 | 6,5,4,3-tetramethyl- |
| 149 | 67 | 6,5,4,4-tetraethyl-3-methyl- |
| 150 | 68 | 6,6,5,5,4,4-hexamethyl- |
| 151 | 69 | 6,6,5,5,4,4,3-heptamethyl- |
| 152 | 70 | 6,6,5,5,4,4,3,3-octamethyl- |

TABLE VI

| EXAMPLE | NUMBER OF EXAMPLE DESCRIBING QUATERNARY SALT STARTING MATERIAL | PRODUCT [(PREFIX LISTED BELOW)-1,3,4,5,6,7,7a,11,12,16b-DECAHYDRO-BENZO[6,7]CYCLOHEPTA[1,2,3-de]-AZEPINO[2,1-a]ISOQUINOLINE] |
|---|---|---|
| 153 | 71 | parent base 1,3,4,5,6,7,7a,11,12,16b-decahydrobenzo[6,7]cyclohepta[1,2,3-de]-azepino[2,1-a]isoquinoline |
| 154 | 72 | 7-methyl- |
| 155 | 73 | 6-methyl- |
| 156 | 74 | 5-methyl- |
| 157 | 75 | 4-methyl- |
| 158 | 76 | 3-methyl- |
| 159 | 77 | 7,7-dimethyl- |
| 160 | 78 | 7,5-diethyl-7-propyl-3-methyl- |
| 161 | 79 | 7,5,4,3-tetraethyl- |
| 162 | 80 | 7-propyl-6,3,3-triethyl-5-methyl- |
| 163 | 81 | 7,7,6,6,5,5-hexamethyl- |
| 164 | 82 | 7,7,6,6,5,5,3-heptamethyl-3-ethyl- |

EXAMPLE 165

To a warm solution of the benzocycloheptaisoquinoline, 1,4,5,6,6a,10,11,15b-octahydro-3H-benzo[6,7]cyclohepta[1,2,3-de]- pyrido[2,1-a]isoquinoline (Isomer B) (0.7 g), described in Example 84, in 18 ml of water, 4 ml of acetic acid and 5 ml of tetrahydrofuran, mercuric acetate (3.08 g) is added portionwise. The mixture is boiled for one hour. Solid mercurous acetate is collected on a filter and the filtrate is rendered alkaline with 10% aqueous sodium hydroxide and extracted with ether. The ether extract is dried, and then treated with gaseous hydrochloric acid. The resulting precipitate is collected and recrystallized from acetone to afford a product identical to 1,3,4,5,6,10,11,15b-octahydrobenzo[6,7]cyclohepta- [1,2,3-de]pyrido[2,1-a]isoquinolinium chloride obtained in Example 2.

The same product is isolated when the corresponding Isomer A, described in Example 85, instead of above Isomer B, is used as the starting material.

In the same manner, but using any of the benzocycloheptaisoquinolines listed in Examples 83, 86 to 164 and 189 to 292, see below, instead of the benzocycloheptaisoquinoline of this Example, the corresponding quaternary salts of formula IV are obtained.

EXAMPLE 166

A mixture of 10,11-dihydro-5H-dibenzo[a,d]cycloheptene- 5-methylamine (20.0 g), 5-chlorovaleric acid chloride (19.2 g) and sodium carbonate (35.0 g) in 250 ml of benzene is stirred and subjected to reflux for 16 hours. The reaction mixture is diluted with water. The benzene layer is separated and washed with water, dried and evaporated to dryness. The residue is crystallized from benzene-hexane to afford the haloamide N-[(10,11-dihydro-5H-dibenzo[a,d]cyclohepten-5-yl)methyl]-5- chlorovaleramide (III, Alk = $CH_2CH_2CH_2CH_2$ and Y = Cl), m.p. 98°–99° C.

The procedure of Example 166 may be followed to make other haloamides of this invention of formula III in which Alk is as defined above and Y is a chlorine by using an appropriate ω-haloalkanoic acid halide, described above, instead of 5-chlorovaleric acid chloride.

The above N-[(10,11-dihydro-5H-dibenzo[a,d]cyclohepten- 5-yl)methyl]-5-chlorovaleramide, and the other haloamides of this invention may be converted to the corresponding quaternary salts of formula IV of this invention for example, the quaternary salts described in Examples 2 to 82, by subjecting said haloamides to the conditions of the Bischler-Napieralski reaction, for example, the conditions described in the procedure of Example 2.

EXAMPLE 167

A solution of chloromethyl methyl ether (40.2 g, 0.5 mole, freshly distilled) in dry tetrahydrofuran (80 ml) is prepared, and about 5 ml of that solution are added to a stirred mixture of magnesium turnings (12.0 g, 0.5 g - atom) and mercuric chloride (500 mg) in tetrahydrofuran (20 ml) until an exothermic reaction ensues. The flask is cooled to 0° ± 10° and the remainder of the chloromethyl methyl ether solution is added dropwise with thorough agitation. After completion of addition a solution of 10,11-dihydro-5H- dibenzo[a,b]cyclohepten-5-one (56.1 g 0.25 mole) in tetrahydrofuran is added dropwise. The reaction mixture is stirred overnight at room temperature and the complex is hydrolyzed with ice-cold ammonium chloride solution. The aqueous layer is extracted with ether (3 × 100 ml) and the combined extracts are washed with sodium chloride solution, dried and evaporated under reduced pressure to give 10,11-dihydro-5-methoxymethyl-5H-dibenzo[a,d]-cyclohepten- 5-ol as an oil with b.p. 143°–144° C/0.05 mm, $\gamma_{max}^{film}$: 3500 cm$^{-1}$, 2820 cm$^{-1}$.

EXAMPLE 168

A solution of 10,11-dihydro-5-methoxymethyl-5H-dibenzo [a,d]cyclohepten-5-ol (52.0 g 0.21 mole) and formic acid (60 ml) is heated under refluxing conditions for three hours. The mixture is cooled, diluted with water (500 ml) and the oil is extracted into benzene. Evaporation of the solvent yields the crude aldehyde as a viscous oil.

The product is stirred overnight at room temperature with a solution of "Girard-T" reagent (40 g) in methanol (400 ml). The precipitate is combined with the residue obtained on evaporation of the methanol. The Girard adduct is dissolved in water and the solution is extracted with ether (6 × 100 ml) to remove non-carbonylic impurities. Hydrolysis of the adduct is effected by stirring the aqueous solution overnight (25°) with 40% sulfuric acid. The precipitated product is filtered off, washed well with water and dried to yield 10,11-dihydro-5H-dibenzo[a,d]- cycloheptene-5-carboxaldehyde as a solid with m.p. 76°–77° C which may be purified by distillation (h.p. 135°–138° C/0.2 - 0.3 mm) or recrystallization from cyclohexane to m.p. 78° C., $\gamma_{max}^{CHCl_3}$: 2700 (C-H stretching); 1720 cm $^{-1}$ (CHO).

The compound is also characterized as the 2,4-dinitro-phenylhydrazone, m.p. 217° C (from acetic acid) $\gamma_{max}^{CHCl}$: 3300 (NH); 1610 (C = N); 1315, 1510 cm$^{-1}$ (NO$_2$).

EXAMPLE 169

By subjecting a mixture of 10,11-dihydro-5H-dibenzo-[a,d]cycloheptene-5-carboxaldehyde (2.2 g), described in Example 168, and 5-aminovaleric acid ethyl ester (1.45 g) and zinc dust (3.0 g) in 3.0 ml of acetic acid and 100 ml of benzene, to a two hour reflux, followed by removal of the excess zinc by filtration, addition of dilute sodium hydroxide solution to render the mixture alkaline and extraction with benzene affords the cyclic amide, N-[(10,11-dihydro-5H-dibenzo[a,d]cyclohepten-5-yl)methyl]-2-piperidone, $\gamma_{max}^{CHCl_3}$ 1650 cm$^{-1}$, as an oil. Further treatment of this oil according to the conditions of the Bischler-Napieralski reaction described in Example 2, yields a product identical with the quaternary salt, 1,3,4,5,6,10,11,15b-octahydrobenzo[6,7]cyclohepta[1,2,3-de]pyrido[2,1-a]isoquinolinium chloride obtained in Example 2.

The procedure of Example 169 may be followed to make other quaternary salts of formula IV, for example, the quaternary salts described in Examples 3 to 82. In each case an equivalent amount of the appropriate amino ester of general formula NH$_2$-Alk-COOR$^{17}$, in which Alk is organic radical A, B or C and R$^{17}$ is a lower alkyl, is used instead of 5-aminovaleric acid ethyl ester.

EXAMPLE 170

The quaternary salt, 1,3,4,5,6,10,11,15b-octahydrobenzo[6,7]cyclohepta[1,2,3-de]pyrido[2,1-a]isoquinolinium chloride (0.001 mole), described in Example 2, is added portionwise to the alkyl magnesium halide, methyl magnesium iodide (0.002 mole) in 100 ml of ether. The reaction mixture is refluxed for 40 minutes. Excess methyl magnesium iodide is destroyed by the slow addition of a saturated solution of ammonium chloride. The ether layer is separated, dried and concentrated to dryness. The residue is subjected to chromatography on alumina (activity-1). Elution with benzene gives 6a-methyl-1,4,5,6,6a,10,11,15b-octahydro-3H-benzo[6,7]-cyclohepta[1,2,3-de]pyrido[2,1-a]isoquinoline (I, R$^1$ = CH$_3$ and Alk = CH$_2$CH$_2$CH$_2$CH$_2$); m.p. 119°–120° C, after recrystallization from hexane. This corresponding hydrochloride acid addition salt of this benzocycloheptaisoquinoline derivative has m.p. 270° C (dec.) after recrystallization from methanol-ether.

The procedure of Example 170 may be followed to prepare the remaining benzocycloheptaisoquinoline derivatives of this invention of formula I in which R$^1$ represents a lower alkyl, by using the appropriate quaternary salt of formula IV, for example the quaternary salts described in Examples 2 to 82, and 165 together with the appropriate lower alkyl magnesium halide. For example, in this manner the 6a-methyl-, 6a-ethyl and 6a-propyl analogs of the benzocycloheptaisoquinoline derivatives described in Examples 83–164 are obtained by using the same quaternary salt starting material employed in those Examples together with the alkyl magnesium halides, methyl, ethyl or propyl magnesium bromide, respectively.

EXAMPLE 171

To freshly distilled 1-buten-3-one (5.4g), 1,7,8,12b-tetrahydrobenzo[1,2]cyclohepta[3,4,5-de]isoquinoline hydrochloride (5.4 g) is added portionwise. The mixture is heated on a steam bath for 30 minutes, becoming homogenous and finally semi-solid. The mixture is diluted with ether and the resulting precipitate is collected on a filter and washed with ether. The precipitate is dissolved in 10% aqueous sodium hydroxide and extracted with ethyl acetate. The extract is dried and evaporated to dryness. The residue is crystallized from acetone-hexane to afford 1,3,4,6,6a,10,11,15b-octahydro-5H-benzo[6,7]cyclohepta[1,2,3-de]pyrido[2,1-a]isoquinolin-5-one, (VIII, R$^{12}$, R$^{13}$, R$^{14}$, R$^{15}$ and R$^{16}$ = H), m.p. 150°–155° C. This product is a mixture of the A and B isomers, which may be separated by chromatography on silica gel. Elution with 20% chloroform in benzene gives 1,3,4,6,6a,10,11,15b-octahydro-5H-benzo[6,7]- cyclohepta[1,2,3-de]pyrido[2,1-a]isoquinolin-5-one (Isomer B), m.p. 202°-203° C after recrystallization from acetone-hexane. Elution with chloroform gives the corresponding Isomer A, m.p. 163°-165° C, after recrystallization from acetone-hexane.

The procedure of Example 171 may be used to prepare other aminoketones of formula VIII. In each case an equivalent amount of an appropriate unsaturated ketone of formula

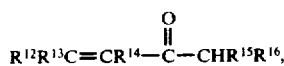

in which $R^{12}$, $R^{13}$, $R^{14}$, $R^{15}$ and $R^{16}$ are as defined in the first instance, is used instead of 1-buten-3-one. Examples of such aminoketones are listed in Table VII together with the appropriate unsaturated ketones used as starting materials.

TABLE VII

| | STARTING MATERIAL $R^{12}R^{13}C=CR^{14}—\overset{O}{\underset{\|}{C}}—CHR^{15}R^{16}$ | | | | | AMINO KETONE PRODUCT (FORMULA VIII) [(Prefix listed below)-1,3,4,6,6a,10,11,15b-OCTAHYDRO-5H-BENZO[6,7]-CYCLOHEPTA[1,2,5-de]PYRIDO[2,1-a]-ISOQUINOLIN- |
|---|---|---|---|---|---|---|
| Example | $R^{12}$ | $R^{13}$ | $R^{14}$ | $R^{15}$ | $R^{16}$ | 5-ONE] |
| 172 | CH₃ | H | H | H | H | 3-methyl- |
| 173 | H | H | CH₃ | H | H | 4-methyl- |
| 174 | H | H | H | CH₃ | H | 6-methyl-;(m.p.181–183° C) |
| 175 | C₂H₅ | H | H | H | H | 3-ethyl- |
| 176 | H | H | C₂H₅ | H | H | 4-ethyl- |
| 177 | H | H | H | C₂H₅ | H | 6-ethyl- |
| 178 | n-C₃H₇ | H | H | H | H | 3-propyl- |
| 179 | H | H | n-C₃H₇ | H | H | 4-propyl- |
| 180 | H | H | H | n-C₃H₇ | H | 6-propyl- |
| 181 | CH₃ | CH₃ | H | H | H | 3,3-dimethyl-;(m.p.185–192° C) |
| 182 | H | H | H | CH₃ | CH₃ | 6,6-dimethyl- |
| 183 | H | H | H | C₂H₅ | C₂H₅ | 6,6-diethyl- |
| 184 | CH₃ | H | H | C₂H₅ | H | 6-ethyl-3-methyl- |
| 185 | CH₃ | CH₃ | H | H | n-C₃H₇ | 3,3-dimethyl-6-propyl- |
| 186 | CH₃ | CH₃ | CH₃ | CH₃ | CH₃ | 3,3,4,6,6-pentamethyl- |
| 187 | H | H | sec-C₄H₇ | H | H | 4-sec-butyl-; (m.p.144–148° C) |
| 188 | CH₃ | H | CH₃ | H | H | 3,4-dimethyl-;(m.p.239–242° C) |

EXAMPLE 189

A solution of the aminoketone, 1,3,4,6,6a,10,11, 15b-octahydro-5H-benzo[6,7]cyclohepta[1,2,3-de]-pyrido[2,1-a]isoquinolin-5-one (Isomer A), (2.0 g), described in Example 171, in 100 ml of tetrahydrofuran is added to a solution of the Grignard reagent, ethyl magnesium iodide, prepared from 0.8 g of magnesium and 5.2 g of ethyl iodide in ether. The reaction mixture is subjected to reflux for half an hour and the excess of the Grignard reagent is destroyed with water. The reaction mixture is extracted with ether. The ether extract is dried and then evaporated to dryness to yield an oily residue. The residue is purified by chromatography on alumina. Elution with benzene-acetone affords the free base, 5-ethyl-1,4,5,6,6a,10,11,15b-octahydro-3H-benzo[6,7]-cyclohepta[1,2,3-de]pyrido[2,1-a]isoquinolin-5-ol, (Isomer A) (I, $R^1$ = H and Alk = CH₂CH₂C(C₂H₅)(OH)CH₂), $\gamma_{max}^{mull}$ 3400 cm⁻¹ (broad). The corresponding hydrochloric acid addition salt of this product has m.p. 263° C (dec.).

In the same manner but using the B isomer instead of the A isomer of 1,3,4,6,6a,10,11,15b-octahydro-5H-benzo[6,7]cyclohepta[1,2,3-de]pyrido-[2,1-a]isoquinolin-5-one, described in Example 171, the B isomer of 5-ethyl-1,4,5,6,6a,10,11,15b-octahydro-3H-benzo[6,7]-cyclohepta[1,2,3-de]pyrido[2,1-a]isoquinolin-5-ol, nmr (CDCl₃) δ4.52 (d,1H); the corresponding hydrochloric acid addition salt of this isomer has m.p. 245°-249° C.

EXAMPLE 190

To 30 ml of a commerical molar solution of the lithium derivative, t-butyllithium, (0.03H) in pentane, 1,3,4,6,6a,10, 11,15b-octahydro-5H-benzo[6,7]cyclohepta[1,2,3-de]pyrido[2,1-a]isoquinolin-5-one (Isomer A), (3.0g., 0.01H) dissolved in 50 ml. of benzene is added dropwise with stirring and cooling. After stirring at room temperature for 2.5 hr., the reaction mixture is decomposed with water. The organic layer is separated, dried over magnesium sulfate and concentrated to give an oil. The oil is dissolved in benzene and subjected to chromagraphy on a column of basic alumina (activity = II). Elution of the column with chloroform-benzene (1:1) gives (±), (5-OH, 15b-H-trans)-5-±-butyl-1,4,5,6,6a,10,11,15b-octahydro-3H-benzo[6,7]cyclohepta[1,2,3-de]pyrido[2,1-a]isoquinolin-5-ol (Isomer A), nmr (CDCl₃) δ4.87 (t,1H). The corresponding hydrochloric acid addition salt of this compound has m.p. 305°-310° C.

The optically active enantiomers of the above compound are prepared and separated by using d-tartaric acid as the resolving agent; (+), (5-OH, 15b-H-trans)-5-t-butyl-1,4,5,6,6a,10,11,15b-octahydro-3H-benzo[6,7]-cyclohepta[1,2,3-de]pyrido[2,1-a]isoquinolin-5-ol (Isomer A), has $[\alpha]_D^{25}$ + 218.5° (c = 1%, methanol); the corresponding (−) enantiomer has $[\alpha]_D^{25}$ −219.0° (c = 1%, methanol).

In the same manner but using the B isomer instead of the A isomer of 1,3,4,6,6a,10,11,15b-octahydro-5H-benzo[6,7]cyclohepta[1,2,3-de]pyrido[2,1-a]isoquinolin-5-one, described in Example 171, the B isomer of the product of this Example is obtained, nmr (CDCl₃) δ4.5 (d,1H). The corresponding hydrochloric acid addition salt of this compound has m.p. 239°-239° C.

EXAMPLE 191

A solution of 1,3,4,6,6*a*,10,11,15*b*-octahydro-5H-benzo[6,7]cyclohepta[1,2,3-de]pyrido[2,1-a]isoquinolin-5-one (Isomer A) (3.0g), described in Example 171, in tetrahydrofuran (70 ml) is added dropwise to a suspension of sodium acetylide in liquid ammonia, prepared from 2.5 g of sodium in 200 ml of ammonia by bubbling acetylene in presence of ferric nitrate as catalyst. The reaction mixture is stirred for 3 hours in a dry ice-acetone bath, then 5 g of ammonium chloride is added and the ammonia is allowed to evaporate at room temperature. Water is added and the residue is extracted with ethyl acetate. The extract is dried over magnesium sulfate, and evaporated to dryness. The residue is crystallized from hexane to give 5-ethynyl-1,4,5,6,6a,10,11,15b-octahydro-3H-benzo[6,7]cyclohepta[1,2,3-de]pyrido[2,1-a]isoquinolin-5-ol (Isomer A)-(I,R$^1$=H and Alk = CH$_2$CH$_2$C(C≡CH)(OH)CH$_2$), m.p. 165°–166° C. The corresponding hydrochloride salt has m.p. 280°–282° C.

In the same manner but using the B isomer instead of the A isomer of 1,3,4,6,6a,10,11,15b-octahydro-5H-benzo[6,7]cyclohepta[1,2,3-de]pyrido[2,1-a]isoquinolin-5-one, described in Example 171, the B isomer of the product of this Example is obtained, m.p. 176°–178° C.

An equivalent amount of potassium acetylide, prepared from potassium instead of sodium, and acetylene, as described above, may replace the sodium acetylide in the procedure of this Example.

EXAMPLE 192

A solution of 5-ethynyl-1,4,5,6,6a,10,11,15b-octahydro-3H-benzo[6,7]cyclohepta[1,2,3-de]pyrido[2,1-a]isoquinolin-5-ol, (Isomer A), described in Example 191, is subjected to hydrogenation using platinum as a catalyst according to the procedure of Example 84. In this manner, 5-ethyl-1,4,5,6,6a,10,11,15b-octahydro-3H-benzo[6,7]cyclohepta[1,2,3-de]pyrido[2,1-a]isoquinolin-5-ol (Isomer A), nmr(CDCl$_3$)δ 4.88 (t,1H), an isomer of the product of the same name obtained in Example 189 with respect to the configuration of the 5-hydroxyl. The corresponding hydrochloride salt of this present isomer has m.p. 212°–214° C.

In the same manner but using the B isomer instead of the A isomer of 5-ethynyl-1,4,5,6,6a,10,11,15b-octahydro-3H-benzo[6,7]cyclohepta[1,2,3-de]pyrido[2,1-a]isoquinolin-5-ol, described in Example 191, there is obtained the B isomer of 5-ethyl-1,4,5,6,6a,10,11,15b-octahydro-3H-benzo[6,7]cyclohepta[1,2,3-de]pyrido[2,1-a]isoquinolin-5-ol, nmr (CDCl$_3$) δ 4.52(d,1H), which is an isomer of the product of the same name obtained in Example 189 with respect to the configuration of the 5-hydroxyl.

The procedure of Examples 189 or 190 may be used to prepare other 5-substituted derivatives of 1,4,5,6,6a,10,11,15b-octahydro-3H-benzo[6,7]cyclohepta[1,2,3-de]pyrido[2,1-a]isoquinolin-5-ol, compounds of formula I in which R$^1$ is hydrogen and Alk is organic radical D in which R$^{12}$, R$^{13}$, R$^{14}$, R$^{15}$ and R$^{16}$ are hydrogen, L is hydroxy and M is as defined in the first instance. An equivalent amount of the appropriate Grignard reagent in the case of the procedure of Example 189, or the appropriate lithium derivative, in the case of the procedure of Example 190, is used, instead of ethyl magnesium iodide or t-butyllithium, respectively. Examples of such 5-substituted compounds prepared in this manner, are listed in Table VIII together with the Grignard or lithium derivative that is used in the Example.

TABLE VIII

| Ex. | Grignard Reagent or Lithium Derivative, starting material | Product(±).(5-OH. 15β-H-trans)-Prefix listed below- 1,4,5,6,6a,10,11,15b-octahydro-3H-benzo[6,7]-cyclohepta[1,2,3-de]pyrido[2,1-a]-isoquinolin-5-ol] | nmr of product. δ(CDCl$_3$) | m.p. of corresponding hydrochloric acid addition salt, °C |
|---|---|---|---|---|
| 193 | n-C$_4$H$_9$Li | 5-butyl- | 4.90 (t, 1H) | 287–289 |
| 194 | CH$_2$=CHCH$_2$MgBr | 5-allyl- | 4.70 (t, 1H) | 280–282 |
| 195 | (CH$_3$)$_2$CHMgCl | 5-isopropyl- | 4.90 (t, 1H) | 282–284 |
| 196 | CH$_3$MgCl | 5-methyl- | 4.92 (t, 1H) | 254–256 |
| 197 | (CH$_2$)$_2$CHLi (cyclopropyl-Li) | 5-cyclopropyl- | 4.92 (t, 1H) | 260–262 |
| 198 | CH$_3$C≡CLi | 5-(1-propynyl)- | 4.54 (t, 1H) | |
| 199 | n-C$_3$H$_7$Li | 5-propyl- | 4.87 (t, 1H) | 290–291 |
| 200 | n-C$_6$H$_{13}$Li | 5-hexyl- | 4.89 (t, 1H) | 285–287 |
| 201 | C$_6$H$_5$-Li | 5-phenyl- | 4.92 (t, 1H) | 290–292 |
| 202 | (CH$_2$)$_5$CHLi (cyclohexyl-Li) | 5-cyclohexyl- | 4.92 (t, 1H) | 312–314 |
| 203 | CH$_2$=CHLi | 5-vinyl- | 4.90 (t, 1H) | |
| 203a | (3,4-di-OCH$_3$)C$_6$H$_3$MgBr | 5-(3,4-dimethoxyphenyl)- | 5.0 (t, 1H) | 227–230 |
| 203b | (2-OCH$_3$)C$_6$H$_4$MgBr | 5-o-anisyl- | 4.98 (t, 1H) | 240–241 |
| 203c | (3-fluoro)C$_6$H$_4$MgBr | 5-m-fluorophenyl- | 4.97 (t, 1H) | 292–294 |
| 203d | (2-chloro)C$_6$H$_4$MgBr | 5-o-chlorophenyl- | 4.96 (t, 1H) | 272–274 |
| 203e | (4-bromo)C$_6$H$_4$MgBr | 5-p-bromophenyl | 5.0 (t, 1H) | 275–278 |
| 203f | (2-CF$_3$)C$_6$H$_4$MgBr | 5-o-trifluoromethylphenyl- | 5.0 (t, 1H) | 224–230 |
| 203g | (2-CH$_3$)C$_6$H$_4$MgBr | 5-o-tolyl- | 4.97 (t, 1H) | 272–275 |
| 203h | (3-OCH$_3$)C$_6$H$_4$MgBr | 5-m-anisyl- | 4.99 (t, 1H) | 272–274 |
| 203i | (4-OCH$_3$)C$_6$H$_4$MgBR | 5-p-anisyl- | 4.98 (t, 1H) | 250–252 |
| 203j | (2-C$_4$H$_3$S)MgBr | 5-(2-thienyl)- | 4.97 (t, 1H) | 249–251 |
| 203k | (3-C$_4$H$_3$S)MgBr | 5-(3-thienyl)- | 4.95 (t, 1H) | 265–267 |
| 203l | (2-C$_4$H$_3$O)Li | 5-(2-furyl)- | 4.92 (t, 1H) | 244–246 |
| 203m | benzyl MgBr | 5-benzyl- | 4.97 (t, 1H) | 255–258 |
| 203n | (3-C$_5$H$_4$N)MgBr | 5-(3-pyridyl) | 4.95 (t, 1H) | 283–285 |

The corresponding B isomers of the products of Examples 193–203n are obtained in the same manner as the A isomers of these Examples by using the B isomer instead of the A isomer of the starting aminoketone of Example 189.

In the same manner as described above, using d-tartaric acid as the resolving agent, the compounds decribed in Table VIII are resolved into their respective optically active enantiomers, some of which are decribed and characterized in Table VIIIa below.

gen or lower alkyl, L is hydroxy and M is as defined in the first instance. Examples of such 5-substituted derivatives are listed in Table X together with the appropriate starting aminoketone which is noted by the Example in which the starting aminoketone is prepared. Also, noted TABLE VIIIa

| Ex. No. | Starting Material, Ex. No. and Name [(+), (5-OH, 15b-H-trans)-Prefix, listed below- 1,4,5,6,6a,10,11,15b-octahydro-3H-benzo[6,7]-cyclohepta[1,2,3-de]-pyrido[2,1-a]isoquinolin-5-ol] | Product [(+) or (−), (5-OH, 15b-H-trans)-Prefix listed below- 1,4,5,6,6a,10,11,15b-octahydro-3H-benzo-[6,7]-cyclohepta[1,2,3-de]pyrido[2,1-a] isoquinolin-5-ol] | $[\alpha]_D^{25}$ 1%, methanol | m.p. of corresponding hydrochloric acid addition salt, °C. |
|---|---|---|---|---|
| 03 o | No. 195, 5-isopropyl- | (+) 5-isopropyl- | + 219.2° | 260–264 |
| 03 p | No. 195, 5-isopropyl- | (−) 5-isopropyl- | − 219.8° | 266–267 |
| 03 q | No. 201, 5-phenyl- | (+) 5-phenyl- | + 232.6° | 232–235 |
| 03 r | No. 201, 5-phenyl- | (−) 5-phenyl- | − 233.3° | 234–235 |
| 03 s | No. 202, 5-cyclohexyl- | (+) 5-cyclohexyl- | + 200.0° | 248–250 |
| 03 t | No. 202, 5-cyclohexyl- | (−) 5-cyclohexyl- | − 199.9° | 248–250 |

The procedure of Example 189 may be used to prepare 5-ethyl derivatives of formula I in which $R^1$ is hydrogen and Alk is organic radical D in which $R^{12}$, $R^{13}$, $R^{14}$, $R^{15}$ and $R^{16}$ are each hydrogen or lower alkyl, L is hydroxy and M is ethyl. Example of such 5-ethyl derivatives are listed below in Table IX. In each case an equivalent amount of the corresponding, starting aminoketone, noted by the Example in which it is prepared, is used instead of 1,3,4,6,6a,10,11,15b-octahydro-5H-benzo[6,7]cyclohepta[1,2,3-de]pyrido[2,1-a]isoquinolin--one.

therein is the appropriate Grignard reagent, in the case of the use of the procedure of Example 189 or lithium derivative, in the case of the use of the procedure of Example 190, which is used in the Example.

For instance, the product of Example 279, (±), (5-OH, 15b-H-trans)-4-sec-butyl-5-isopropyl-1,4,5,6,6a,10,11,15b-octahydro-3H-benzo[6,7]cyclohepta[1,2,3,-de]pyrido[2,1-a]isoquinolin-5-ol; nmr (CDCl$_3$) δ 5.00 (m, 1H), is obtained by using the aminoketone of Example 187 and the lithium derivative, isopropyllithium, in the case of using the procedure of Example

TABLE IX

| Example | No. of the Example in which starting amino-ketone is prepared | Product [(±), (5-OH, 15b-H-trans)-Prefix listed below- 1,4,5,6,6a,10,11, 15b-octahydro-3H-benzo[6,7]-cyclohepta[1,2,-3-de]pyrido[2,1-a]isoquinolin-5-ol] | nmr of Product δ (CDCl$_3$) | m.p. of corresponding hydrochloric acid addition salt, °C |
|---|---|---|---|---|
| 204 | 181 | 5-ethyl-3,3-dimethyl- | 4.77(d,1H) | 285–286 |
| 205 | 188 | 5-ethyl-3,4-dimethyl- | 4.88(d,1H) | 278–282 |
| 206 | 174 | 5-ethyl-6-methyl- | 4.42(d,1H) | 215–218 |
| 207 | 187 | 4-sec-butyl-5-ethyl- | 4.57(d,1H) | |

The procedure of Examples 189 or 190 may be followed to prepare other 5-substituted derivatives of formula I in which $R^1$ is hydrogen and Alk is organic radical D in which $R^{12}$, $R^{13}$, $R^{14}$, $R^{15}$ and $R^{16}$ are each hydrogen or lower alkyl, L is hydroxy and M is as defined in 190 as described above. The corresponding hydrochloric acid addition salt of this product has m.p. 250°–256° C.

TABLE X

| EXAMPLE | No. of the Example in which the starting aminoketone is prepared | Grignard reagent or lithium derivative, starting material | Product [(±), (5-OH, 15b-H-trans) Prefix listed below-1,4,5,6,6a,10, 11,15b-octahydro-3H-benzo[6,7]-cyclohepta[1,2,3-de]pyrido[2,1-a] isoquinolin-5-ol] |
|---|---|---|---|
| 203 | 172 | C$_2$H$_5$Li | 5-ethyl-3-methyl- |
| 209 | 172 | CH$_2$=C(CH$_3$)CH$_2$MgCl | 3-methyl-5-(2-methallyl)- |
| 210 | 172 | CH$_3$C≡CLi | 3-methyl-5-(1-propynl)- |
| 211 | 172 | (CH$_2$)$_3$CHMgBr (cyclobutyl) | 5-cyclobutyl-3-methyl- |
| 212 | 172 | (CH$_2$)$_5$C(CH$_3$)Li* (1-methylcyclohexyl) | 3-methyl-5-(1-methylcyclohexyl)- |
| 213 | 172 | C$_6$H$_5$—MgBr | 3-methyl-5-phenyl- |
| 214 | 173 | n-C$_3$H$_7$MgCl | 4-methyl-5-propyl- |
| 215 | 173 | CH$_2$=CHLi | 4-methyl-5-vinyl- |
| 216 | 173 | HC≡C—CH$_2$Li | 4-methyl-5-(2-propynyl)- |

TABLE X-continued

| EXAMPLE | No. of the Example in which the starting aminoketone is prepared | Grignard reagent or lithium derivative, starting material | Product [(±), (5-OH, 15b-H-trans) Prefix listed below-1,4,5,6,6a,10,11,15b-octahydro-3H-benzo[6,7]-cyclohepta[1,2,3-de]pyrido[2,1-a]isoquinolin-5-ol] |
|---|---|---|---|
| 217 | 173 | cyclopentyl-CHLi ((CH₂)₄CHLi, ring) | 5-cyclopentyl-4-methyl- |
| 218 | 173 | (CH₂)₄C(C₂H₅)Li* (ring) | 5-(1-ethylcyclopentyl)-4-methyl- |
| 219 | 173 | C₆H₅—MgBr | 4-methyl-5-phenyl- |
| 220 | 174 | CH₂=CHCH₂Li | 5-allyl-6-methyl- |
| 221 | 174 | HC≡CLi | 5-ethynyl-6-methyl- |
| 222 | 174 | (CH₂)₂CHLi (ring) | 5-cyclopropyl-6-methyl- |
| 223 | 174 | (CH₂)₂C(CH₃)Li* (ring) | 6-methyl-5-(1-methylcyclopropyl)- |
| 224 | 175 | t-C₄H₉Li | 5-t-butyl-3-ethyl- |
| 225 | 175 | CH₂=CHCH₂MgBr | 5-allyl-3-ethyl- |
| 226 | 175 | HC≡CLi | 3-ethyl-5-ethynyl- |
| 227 | 175 | (CH₂)₂CHLi (ring) | 5-cyclopropyl-3-ethyl- |
| 228 | 175 | (CH₂)₃C(n-C₃H₇)Li* (ring) | 3-ethyl-5-(1-propylcyclobutyl)- |
| 229 | 175 | C₆H₅—MgBr | 3-ethyl-5-phenyl |
| 230 | 176 | C₂H₅MgI | 4,5-diethyl- |
| 231 | 176 | CH₂=C(CH₃)CH₂MgCl | 4-ethyl-5-(2-methallyl)- |
| 232 | 176 | HC≡CCH₂Li | 4-ethyl-5-(2-propynyl)- |
| 233 | 176 | (CH₂)₅CHLi (ring) | 5-cyclohexyl-4-ethyl- |
| 234 | 176 | (CH₂)₅C(C₂H₅)Li* (ring) | 4-ethyl-5-(1-ethylcyclohexyl)- |
| 235 | 177 | n-C₃H₇Li | 6-ethyl-5-propyl- |
| 236 | 177 | CH₂=CHCH₂MgBr | 5-allyl-6-ethyl- |
| 237 | 177 | HC≡CLi | 6-ethyl-5-ethynyl- |
| 238 | 177 | (CH₂)₂CLi (ring) | 5-(cyclopropyl)-6-ethyl- |
| 239 | 177 | (CH₂)₃C(CH₃)Li* (ring) | 6-ethyl-5-(1-methylcyclopropyl)- |
| 240 | 178 | n-C₃H₇MgI | 3,5-dipropyl- |
| 241 | 178 | CH₂=CHCH₂Br | 5-allyl-3-propyl- |
| 242 | 178 | (CH₂)₄CLi (ring) | 5-cyclopentyl-3-propyl- |
| 243 | 178 | (CH₂)₄C(C₂H₅)Li* (ring) | 5-(1-ethylcyclopentyl)-3-propyl- |
| 244 | 179 | CH₃MgBr | 5-methyl-4-propyl- |

TABLE X-continued

| EXAMPLE | No. of the Example in which the starting aminoketone is prepared | Grignard reagent or lithium derivative, starting material | Product [(±), (5-OH, 15b-H-trans) Prefix listed below-1,4,5,6,6a,10,11,15b-octahydro-3H-benzo[6,7]-cyclohepta[1,2,3-de]pyrido[2,1-a]isoquinolin-5-ol] |
|---|---|---|---|
| 245 | 179 | $CH_3CH=CHMgBr$ | 4-propyl-5-(propenyl)- |
| 246 | 179 | $(CH_2)_2CHLi$ (cyclic) | 5-cyclopropyl-4-propyl- |
| 247 | 179 | $(CH_2)_2C(CH_3)Li^*$ (cyclic) | 5-(1-methylcyclopropyl)-4-propyl- |
| 248 | 180 | $n-C_3H_7Li$ | 5,6-diisopropyl- |
| 249 | 180 | $CH=CHCH_2MgBr$ | 5-allyl-6-propyl- |
| 250 | 180 | $(CH_2)_4CHLi$ (cyclic) | 5-cyclopentyl-6-propyl- |
| 251 | 180 | $(CH_2)_4C(CH_3)Li^*$ (cyclic) | 5-(1-methylcyclopentyl)-6-propyl- |
| 252 | 181 | $CH_3MgI$ | 3,3,5-trimethyl- |
| 253 | 181 | $CH_2=CHLi$ | 3,3-dimethyl-5-vinyl- |
| 254 | 181 | $CH_3C\equiv CLi$ | 3,3-dimethyl-5-(1-propynyl)- |
| 255 | 181 | $(CH_2)_2CHLi$ (cyclic) | 5-cyclopropyl-3,3-dimethyl- |
| 256 | 182 | $(CH_2)_2C(CH_3)Li^*$ (cyclic) | 3,3-dimethyl-5-(1-methylcyclopropyl)- |
| 257 | 182 | —Li | 3,3-dimethyl-5-phenyl- |
| 258 | 182 | $n-C_3H_7MgI$ | 6,6-dimethyl-5-propyl- |
| 259 | 182 | $CH_2=CHCH_2MgBr$ | 5-allyl-6,6-dimethyl- |
| 260 | 183 | $(CH_2)_5CHMgCl$ (cyclic) | 5-cyclohexyl-6,6-dimethyl- |
| 261 | 183 | $(CH_2)_5C(C_2H_5)Li^*$ (cyclic) | 5-(1-ethylcyclohexyl)-6,6-dimethyl |
| 262 | 183 | $CH_3Li$ | 6,6-diethyl-5-methyl |
| 263 | 183 | $CH_2=C(CH_3)CH_2MgCl$ | 6,6-diethyl-5-(2-methallyl)- |
| 264 | 183 | $(CH_2)_2CHMgBr$ (cyclic) | 5-cyclopropyl-6,6-diethyl- |
| 265 | 183 | $(CH_2)_2C(CH_3)Li^*$ (cyclic) | 6,6-diethyl-5-(1-methylcyclopropyl)- |
| 266 | 183 | —Li | 6,6-diethyl-5-phenyl- |
| 267 | 184 | $C_2H_5Li$ | 5,6-diethyl-3-methyl- |
| 268 | 184 | $CH_2=CHLi$ | 6-ethyl-3-methyl-5-vinyl- |
| 269 | 184 | $(CH_2)_3CHLi$ (cyclic) | 5-cyclobutyl-6-ethyl-3-methyl- |
| 270 | 184 | $(CH_2)_2C(n-C_3H_7)Li^*$ (cyclic) | 6-ethyl-3-methyl-5-(1-propylcyclopropyl)- |
| 271 | 185 | $CH_3MgI$ | 3,3,5-trimethyl-6-propyl- |
| 272 | 185 | $CH_2=CHCH_2MgBr$ | 5-allyl-3,3-dimethyl-6-propyl |

TABLE X-continued

| EXAMPLE | No. of the Example in which the starting aminoketone is prepared | Grignard reagent or lithium derivative, starting material | Product [(±), (5-OH, 15b-H-trans) Prefix listed below-1,4,5,6,6a,10,11,15b-octahydro-3H-benzo[6,7]-cyclohepta[1,2,3-de]pyrido[2,1-a]isoquinolin-5-ol] |
|---|---|---|---|
| 273 | 185 | (CH₂)₂CHLi ⌐⌐ | 5-cyclopropyl-3,3-dimethyl-6-propyl- |
| 274 | 185 | (CH₂)₂C(CH₃)Li ⌐⌐ | 3,3-dimethyl-5-(1-methylcyclopropyl)-6-propyl- |
| 275 | 186 | CH₃MgI | 3,3,4,5,6,6-hexamethyl- |
| 276 | 185 | CH₂=CHMgBr | 3,3,4,6,6-pentamethyl-5-vinyl- |
| 277 | 186 | HC≡CLi | 5-ethyl-3,3,4,6,6-pentamethyl- |
| 278 | 186 | (CH₂)₄CHLi ⌐⌐ | 5-cyclopentyl-3,3,4,6,6-pentamethyl- |
| 279 | 187 | i-C₃H₇Li | 4-sec-butyl-5-isopropyl- |
| 280 | 187 | HC≡CLi | 4-sec-butyl-5-ethynyl- |
| 281 | 187 | (CH₂)₂CHLi ⌐⌐ | 4-sec-butyl-5-cyclopropyl- |
| 282 | 187 | (CH₂)₂C(CH₃)Li* ⌐⌐ | 4-sec-butyl-5-(1-methylcyclopropyl)- |
| 283 | 188 | CH₂=CHLi | 3,4-dimethyl-5-vinyl- |
| 284 | 188 | HC≡CLi | 5-ethynyl-3,4-dimethyl- |
| 285 | 188 | (CH₂)₂CHLi ⌐⌐ | 5-cyclopropyl-3,4-dimethyl- |
| 286 | 188 | (CH₂)₂C(CH₃)Li* ⌐⌐ | 3,4-dimethyl-5-(methylcyclopropyl)- |
| 287 | 171 | (CH₂)₃CHLi ⌐⌐ | 5-cyclobutyl- |
| 288 | 171 | (CH₂)₂C(n-C₃H₇)Li* ⌐⌐ | 5-(1-propylcyclopropyl)- |
| 289 | 171 | (CH₂)₃C(C₂H₅)Li* ⌐⌐ | 5-(1-ethylcyclobutyl)- |
| 290 | 171 | (CH₂)₄C(CH₃)Li* ⌐⌐ | 5-(1-methylcyclopentyl)- |
| 291 | 171 | (CH₂)₅C(CH₃)Li* ⌐⌐ | 5-(1-methylcyclohexyl)- |
| 292 | 171 | (CH₂)₂C(CH₃)Li* ⌐⌐ | 5-(1-methylcyclopropyl)- |

Prepared from the corresponding bromide derivatives according to the method of R. G. Jones and H. Gilman, Organic Reactions, 6, 352 (1951). The corresponding cyclobutyl, cyclopentyl and cyclohexyl bromides are prepared by the method of J. G. Traynham and O. S. Pascual, J. Org. Chem., 21, 1362 (1956); the corresponding cyclopropyl bromides are prepared by the method of B. C. Anderson, J. Org. Chem. 27, 2720 (1962) using methallyl chloride, 2-methylbutenyl chlor ide [H. Hoberg, Annalen der Chemie, 656, 1 (1962)] and 2-methylpent-2-enyl chloride [M. B. Evans et al., J. Chem. Soc., 5045 (1962)] as starting materials for the 1-methyl-1-ethyl- and 1-propylcyclopropyl bromides, respectively.

EXAMPLE 293

A mixture of 5-ethyl-1,4,5,6,6a,10,11,15b-octahydro-3H-benzo[6,7]cyclohepta[1,2,3-de]pyrido[2,1-a]isoquinolin-5-ol (Isomer A) (1.5g), described in Example 189 and anhydrous sodium acetate (0.6g) in acetic anhydride is heated at 130° C for 16 hrs. The reaction mixture is cooled, diluted with benzene and water. The benzene layer is separated, washed with sodium carbonate solution and water and then dried over magnesium sulfate. Concentration of the benzene extract affords (±), (5-OH, 15b-H-trans)-5-ethyl-1,4,5,6,6a,10,11,15b-octahydro-3H-benzo[6,7]cyclohepta[1,2,3-de]-pyrido[2,1-a]isoquinolin-5-ol acetate as an oil, $\gamma_{max}^{CHCl_3}$ 1735 cm$^{-1}$. The corresponding hydrochloric acid addition salt has m.p. 238°–240° C after recrystallization from isopropanol-ether.

The procedure of Example 293 may be followed to prepare other acylated derivatives of formula I in which Alk is organic radical D in which L is lower alkanoyloxy. In each case, the amounts of the appropriate 5-substituted-1,4,5,6,6a,10,11,15b-octahydro-3H-benzo[6,7]cyclohepta[1,2,3-de]pyrido[2,1-a]isoquinolin-5-ol, for instance those prepared in Examples 189–292, and the acyl anhydride are equivalent to the amounts of 5-ethyl-1,4,5,6,6a,10,11,15b-octahydro-3H-benzo[6,7]-cyclohepta[1,2,3-de]pyrido[2,1-a]isoquinolin-5-ol and acetic anhydride used in Example 293. For example, (±), (5-OH, 15b-H-trans)-5-ethyl-1,4,5,6,6a,10,11,15b-octahydro-3H-benzo[6,7]cyclohepta[1,2,3-de]-pyrido[2,1-a]isoquinolin-5-ol heptanoate, $\gamma_{max}^{CHCl_3}$ 1731 cm$^{-1}$, may be obtained by replacing acetic anhydride with an equivalent amount of heptanoic anhydride in the procedure of Example 293. Again, for example, 5-t-butyl-1,4,5,6,6a,10,11,15b-octahydro-3H-benzo[6,7]-cyclohepta[1,2,3-de]pyrido[2,1-a]isoquinolin-5-ol acetate (Isomer A), nmr(CDCl$_3$) 2.12(s,3H)4.86(t,1H), may be obtained by replacing 5-ethyl-1,4,5,6,6a,10,11,15b-octahydro-3H-benzo[6,7]cyclohepta[1,2,3-de]-pyrido[2,1-a]isoquinolin-5-ol with an equivalent amount of the corresponding 5-t-butyl analog (Isomer A), prepared as described in Example 190, in the procedure of Example 293. The hydrochloric acid addition salt of (±), (5-OH, 15b-H-trans)-5-±-butyl-1,4,5,6,6a,10,11,15b-octahydro-3H-benzo[6,7]cyclohepta[1,2,3-de]pyrido[2,1-a]isoquinolin-5-ol acetate (Isomer A) has m.p. 228°–229° C.

EXAMPLE 294

A solution of 1,3,4,6,6a,10,11,15b-octahydro-5H-benzo[6,7]cyclohepta[1,2,3-de]pyrido[2,1-a]isoquinolin-5-one (3.0 g), described in Example 171 in 50 ml of acetic acid, 3.0 ml of ethanedithiol and 3.0 ml of boron trifluoride etherate is left at room temperature for 18 hours and then poured on water and extracted with ether. The organic phase is washed to neutral with a saturated solution of sodium carbonate, dried with magnesium sulfate and concentrated to dryness. The residue is triturated with ether and the solid collected yielding 1,3,4,6,6a,10,11,15b-octahydro-5H-benzo [6,7]cyclohepta[1,2,3-de]pyrido[2,1-a]isoquinolin-5-one ethylene dithioketal, m.p. 220°–225° C.

If desired this product may be separated into its A and B isomers by chromatography on silica gel. The corresponding Isomer B has m.p. 150° after elution with chloroform and recrystallization from methanol-hexane and the corresponding Isomer A, has m.p. 225°–230° C after elution with methanol and recrystallization from methanol-hexane.

The procedure of Example 294 may be followed to prepare the corresponding ethylene dithioketals of the other aminoketones of ketones of formula VIII of this invention, listed in Examples 172–188. In each case the appropriate aminoketone is used as starting material instead of 1,3,4,6,6a,10,11,15b-octahydro-5H-benzo[6,7]cyclohepta[1,2,3-de]pyrido[2,1-a]isoquinolin-5-one.

EXAMPLE 295

To a boiling solution of 1,3,4,6,6a,10,11,15b-octahydro-5H-benzo[6,7]cyclohepta[1,2,3-de]pyrido[2,1-a]isoquinolin-5-one ethylene dithioketal (17.0 g), described in Example 294 in 1000 ml of tetrahydrofuran, Raney nickel (170 g) is added portionwise and the reaction mixture is refluxed for six hours. After decanting and concentrating to a minimum volume, it is poured on water and extracted with ether, dried and concentrated to an oil. This oil is dissolved in ether and treated with gaseous hydrochloric acid. The resulting precipitate is recrystallized from isopropanol-acetone to yield a product identical with 1,4,5,6,6a,10,11,15b-octahydro-3H-benzo[6,7]cyclohepta[1,2,3-de]pyrido[2,1-a]isoquinoline (Isomer A) hydrochloride described in Example 85.

The procedure of Example 295 may be followed to prepare other benzocycloheptaisoquinolines of formula I listed in Table XI. In each case an equivalent amount of the appropriate thioketal of the aminoketones listed in Table VII, prepared according to the procedure described in Example 294, is used as the thioketal starting material instead of 1,3,4,6,6a,10,11,15b-octahydro-5H-benzo[6,7]cyclohepta[1,2,3-de]pyrido[2,1-a]isoquinolin-5-one ethylene dithioketal.

TABLE XI

| EXAMPLE | STARTING MATERIAL [(PREFIX LISTED BELOW)-1,3,4,6,6a,10,11,15b-OCTAHYDRO-5H-BENZO[6,7]-CYCLOHEPTA[1,2,3-de]-PYRIDO[2,1-a]ISOQUINOLIN-5-ONE ETHYLENE DIETHIOKETAL] | PRODUCT [(PREFIX LISTED BELOW)-1,4,5,6,6a,10,11,15b-OCTA-HYDRO-3H-BENZO[6,7]CYCLO-HEPTA[1,2,3-de]PYRIDO[2,1-a]-ISOQUINOLINE HYDROCHLORIDE] |
|---|---|---|
| 296 | 3-methyl- | 3-methyl- |
| 297 | 4-methyl- | 4-methyl- |
| 298 | 6-methyl- | 6-methyl- |
| 299 | 3-ethyl- | 3-ethyl- |
| 300 | 4-ethyl- | 4-ethyl- |
| 301 | 6-ethyl- | 6-ethyl- |
| 302 | 3-propyl- | 3-propyl- |
| 303 | 4-propyl- | 4-propyl- |

TABLE XI-continued

| EXAMPLE | STARTING MATERIAL [(PREFIX LISTED BELOW)-1,3,4,6,6a,10,11,15b-OCTAHYDRO-5H-BENZO[6,7]-CYCLOHEPTA[1,2,3-de]-PYRIDO[2,1-a]ISOQUINOLIN-5-ONE ETHYLENE DIETHIOKETAL] | PRODUCT [(PREFIX LISTED BELOW)-1,4,5,6,6a,10,11,15b-OCTA-HYDRO-3H-BENZO[6,7]CYCLO-HEPTA[1,2,3-de]PYRIDO[2,1-a]-ISOQUINOLINE HYDROCHLORIDE] |
|---|---|---|
| 304 | 6-propyl- | 6-propyl- |
| 305 | 3,3-dimethyl- | 3,3-dimethyl- |
| 306 | 6,6-dimethyl- | 6,6-dimethyl- |
| 307 | 6,6-diethyl- | 6,6-diethyl- |
| 308 | 6-ethyl-3-methyl- | 6-ethyl-3-methyl- |
| 309 | 3,3-dimethyl-6-propyl | 3,3-dimethyl-6-propyl |
| 310 | 3,3,4,6,6-pentamethyl- | 3,3,4,6,6-pentamethyl- |
| 311 | 4-sec-butyl- | 4-sec-butyl- |
| 312 | 3,4-dimethyl | 3,4-dimethyl |

EXAMPLE 313

To a suspension of 1,3,4,6,6a,10,11,15b-octahydro-5H-benzo[6,7]cyclohepta[1,2,3-de]pyrido[2,1-a]isoquinolin-5-one isomer A (2.0 g), described in Example 171, in 50 ml of methanol, sodium borohydride (2.5 g) is added portionwise. The mixture is heated under refluxing conditions for one hour. After removal of the methanol under vacuum, water is added and the mixture is extracted with ethyl acetate. The extract is dried, concentrated to dryness. The residue is crystallized from ether-hexane to afford the free base, 1,4,5,6,6a,10,11,15b-octahydro-3H-benzo[6,7]cyclohepta[1,2,3-de]pyrido[2,1-a]isoquinolin-5-ol, isomer A, m.p. 157°-159° C. The corresponding hydrochloric acid addition salt of this free base has m.p. 290°-295° C.

The corresponding acetic acid ester is prepared by reacting the above alcohol with acetic anhydride in presence of pyridine. The resulting 5-acetoxy-1,4,5,6,6a,10,11,15b-octahydro-3H-benzo[6,7]cyclohepta[1,2,3-de]pyrido[2,1-a]isoquinoline is characterized by its nmr spectrum showing a CH$_3$CO chemical shift at 2.1 δ (CDCl$_3$). Its hydrochloride salts melts at 265°-270° C.

Using the isomer B of 1,3,4,6,6a,10,11,15b-octahydro-5H-benzo[6,7]cyclohepta[1,2,3-de]pyrido[2,1-a]isoquinolin-5-one described in Example 171, the corresponding alcohol B, m.p. 137°-140° is isolated. The hydrochloric acid addition salt of this free base melts at 280°-285° C.

These free bases may be converted to their corresponding tosylates or mesylates and reduced with lithium aluminum hydride or sodium amalgam, according to the methods described by Fieser and Fieser, cited above, pp. 292-294, see also O. H. Wheeler in "The Chemistry of the Carbonyl Group", cited above, to give a compound identical to 1,4,5,6,6a,10,11,15b-octahydro-3H-benzo[6,7]cyclohepta [1,2,3-de]pyrido[2,1-a]isoquinoline (isomer A or isomer B, respectively) described in Example 85.

The procedure of Example 313 may be followed to prepare the products listed in Table XI, for example, the product of Example 311. In each case the appropriate starting material, an aminoketone product listed in Table VII, for example, the product of Example 187, is reduced to the corresponding 5-alcohol, for example, 4-sec-butyl-1,4,5,6,6a,10,11,15b-octahydro-3H-benzo[6,7]cyclohepta[1,2,3-de]pyrido[2,1-a]isoquinolin-5-ol[nmr δ (CDCl$_3$) 4.52(d,1H); the corresponding hydrochloric acid addition salt has m.p. 272°-280° C.], converted to its corresponding tosylate or mesylate, and reduced again according to the above procedure.

The procedure of the first part of Example 313 may be followed to prepare other 5-alcohols listed in Table XII, instead of 1,4,5,6,6a,10,11,15b-octahydro-3H-benzo[6,7]cyclohepta[1,2,3-de]pyrido[2,1-a]isoquinolin-5-ol. In each case an equivalent amount of appropriate starting material, an aminoketone product listed in Table VII is reduced with sodium borohydride to yield the corresponding 5-alcohol as product, as shown in the following Table XII.

TABLE XII

| EXAMPLE | STARTING MATERIAL [(PREFIX LISTED BELOW)-1,3,4,6,6a,10,11,15b-OCTAHYDRO-5H-BENZO[6,7]-CYCLOHEPTA[1,2,3-de]PYRIDO[2,1-a]ISOQUINOLIN-5-ONE | CORRESPONDING 5-ALCOHOL PRODUCT [(PREFIX LISTED BELOW)-1,4,5,6,6a,10,11,15b-OCTA-HYDRO-3H-BENZO[6,7]CYCLO-HEPTA[1,2,3-de]PYRIDO]-a]-ISOQUINOLIN-5-OL] |
|---|---|---|
| 314 | 3-methyl- | 3-methyl- |
| 315 | 4-methyl- | 4-methyl- |
| 316 | 6-methyl- | 6-methyl- |
| 317 | 3-ethyl- | 3-ethyl- |
| 318 | 4-ethyl- | 4-ethyl- |
| 319 | 6-ethyl- | 6-ethyl- |
| 320 | 3-propyl- | 3-propyl- |
| 321 | 4-propyl- | 4-propyl- |
| 322 | 6-propyl- | 6-propyl- |
| 323 | 3,3-dimethyl- | 3,3-dimethyl- |
| 324 | 6,6-dimethyl- | 6,6-dimethyl- |
| 325 | 6,6-diethyl- | 6,6-diethyl- |
| 326 | 6-ethyl-3-methyl- | 6-ethyl-3-methyl- |
| 327 | 3,3-dimethyl-6-propyl | 3,3-dimethyl-6-propyl |
| 328 | 3,3,4,6,6-pentamethyl- | 3,3,4,6,6-pentamethyl- |
| 329 | 4-sec-butyl- | 4-sec-butyl- |
| 330 | 3,4-dimethyl- | 3,4-dimethyl- |

EXAMPLE 331

5-Ethyl-1,4,5,6,6a,10,11,15b-octahydro-3H-benzo[6,7]cyclohepta[1,2,3-de]pyrido[2,1-a]isoquinolin-5-ol (Isomer A), described in Example 189, may be dehydrated according to the conditions described by R. B. Wagner and H. D. Zook, in "Synthetic Organic Chemistry", John Wiley and Sons, New York, 1953, pp. 32-35, preferably with p-toluenesulphonic acid in benzene solution, followed by hydrogenation according to the conditions described in above Example 84, to give 5-ethyl-1,4,5,6,6a,10,11,15b-octahydro-3H-benzo[6,7]cyclohepta[1,2,3-de]pyrido[2,1-a]isoquinoline, $\lambda_{max}^{ETOH}$ 263 μ (ε = 582) and 270 μ ε = 490).

The procedure of Example 331 may be followed to prepare 5-methyl- and 5-propyl-1,4,5,6,6a,10,11,15b-octahydro-3H-benzo[6,7]cyclohepta[1,2,3-de]pyrido[2,1-a]isoquinoline. In each case the 5-ethyl-1,4,5,6,6a,10,11,15b-octahydro-3H-benzo[6,7]cyclohepta[1,2,3-de]pyrido[2,1-a]isoquinolin-5-ol is replaced by an equivalent amount of the 5-methyl analog, described in Example 196, or the 5-propyl analog, described in Example 199, respectively.

Also, the procedures of Example 189 and 331 may be followed in sequence to prepare the 5-methyl-, 5-ethyl- and 5-propyl-derivatives of the aminoketone products listed in Table XI. In each case the appropriate starting material, an aminoketone product listed in Table VII, is reacted with methyl, ethyl or propyl magnesium bromide, respectively, and the resulting free base containing a hydroxyl group is dehydrated and hydrogenated according to the above procedure.

In the same manner as described in the preceding Examples 1 to 331, inclusive, but replacing the starting materials of formulae II, V and VII with the corresponding starting materials of formulae IIa, Va, and VIIa, the benzo[5,6]cycloheptaisoquinoline derivatives of formula Ia corresponding to the benzo[6,7]cycloheptaisoquinolines of formula I, described in the preceding examples, are obtained. This latter aspect of this invention is illustrated further in the following Examples 332 to 354, inclusive.

EXAMPLE 332

10,11-Dihydro-5H-dibenzo[a,d]cycloheptene-10-methylamine, $\gamma_{max}^{CHCl_3}$ 3390, 3300 cm$^{-1}$, (52.3g, 0.234 mole), is combined with δ-valerolactone (35g, 0.35 mole). The mixture is heated for 2 hr. at 150° C (oil bath temperature). After partial cooling, ethanol (250 ml) is added followed by a solution of potassium carbonate (50 g, 0.36 mole) in water (150 ml). The two-phase mixture is stirred at 60° C overnight. The ethanol is removed under reduced pressure and the residual mixture extracted with chloroform. The chloroform solution is washed with water, dried and taken to dryness. The residue is crystallized from benzene (750 ml) - ether (ca 800 ml) affording N-[(10,11-dihydro-5H-dibenzo[a,d]cyclohepten-10-yl)methyl]-5-hydroxyvaleramide, m.p. 96°-98° C, $\gamma_{max}^{CHCl_3}$ 3630, 3445, 3350, 1663 cm$^{-1}$.

By following the procedure of this example but replacing δ-valerolactone with any of the remaining lactones listed in Example 1, the corresponding N-[(10,11-dihydro-5H-dibenzo[a,d]cyclohepten-10-yl)methyl]hydroxyamides of formula IIIa, corresponding to the hydroxyamides of formula III listed in Example 1, are obtained.

EXAMPLE 333

N-[(10,11-dihydro-5H-dibenzo[a,d]cyclohepten-10-yl)methyl]-5-hydroxyvaleramide (25.0 g, 0.077 mole), described in Example 332, is combined with phosphorus oxychloride (250 ml) and the mixture refluxed for 3 hr. Excess POCl$_3$ is removed under reduced pressure, the residue taken up in ethanol (250 ml), saturated aqueous sodium hydroxide (30 - 35 ml) added to pH 8 - 9, followed by water (75 ml). The mixture is stirred at reflux temperature for one hour, then concentrated HCl (100 ml) is added. A clear solution is obtained by addition of more ethanol (100 ml) and water (100 ml). To the hot solution Zn powder (30 g) is added in portions during 0.5 hr. stirred at reflux temperature for 3.5 hr. The solution is decanted from undissolved Zn and the Zn is washed with hot ethanol. The combined ethanol solutions are evaporated. The residue is treated with aqueous NH$_4$OH (d=1.9, 200 ml) and the oily precipitate extracted with chloroform-ether. The organic solution is washed with water, dried and taken to dryness. The residue is subjected to chromatography on neutral alumina (1200 g). Elution with hexane-benzene (8.5:1.5), followed by hexane-benzene (3:2), gives 1,4,5,6,6a,10,15,15a-octahydro-3H-benzo[5,6]cyclohepta[1,2,3-de]pyrido[2,1-a]isoquinoline (Isomer A), m.p. 127°-130° C, nmr (CDCl$_3$) δ2.95 (7H), 5.37 (1H), after recrystallization from benzene-pentane. Further elution with benzene gives 1,4,5,6,6a,10,15,15a-octahydro-3H-benzo[5,6]cyclohepta[1,2,3-de]pyrido[2,1-a]isoquinoline (Isomer B), m.p. 120°-124° C, nmr (CDCl$_3$) δ2.95 (7H), 5.52 (1H), after recrystallization from benzene-pentane. The corresponding hydrochloric acid addition salt of the free base (Isomer A) of this example has m.p. 270°-275° C and the corresponding hydrochloric acid addition salt of the free base (Isomer B) has m.p. 275°-280° C.

In another experiment according to the procedure of this example, the residue, obtained after removal of excess POCl$_3$ under reduced pressure, is twice taken to dryness from dry toluene whereby the residue turned insoluble in this solvent. The residue is dissolved in a little methanol and diluted with benzene. The benzene solution is washed quickly with aqueous sodium bicarbonate solution (twice) and saturated NaCl solution, dried (MgSO$_4$) and distilled at atmospheric pressure to about half of its original volume of ca. 450 ml. During the distillation a fine, solid precipitate occurs, which is collected, washed with benzene and ether to give the intermediate quaternary salt, 1,3,4,5,6,10,15,15a-octahydrobenzo[5,6]cyclohepta[1,2,3-de]pyrido[2,1-a]isoquinolinium chloride, m.p. 225°-235° C, $\gamma_{max}^{CHCl_3}$ 1652, 1580, 1490 cm$^{-1}$.

By following the procedure of this example but replacing N-[(10,11-dihydro-5H-dihenzo[a,d]cyclohepten-10-yl)methyl]-5-hydroxyvaleramide with any of the remaining N-[(10,11-dihydro-5H-dibenzo[a,d]cyclohepten-10-yl)methyl]hydroxyamides, prepared as described in Example 332, the corresponding A and B isomers of the benzocycloheptaisoquinolines of formula Ia are obtained via the corresponding quaternary salts.

EXAMPLE 334

A mixture of formic acid and acetic anhydride (1:1, 20 ml) is prepared at 0° to 10° C and added to 10,11-dihydro-5H-dibenzo[a,d]cycloheptene-10-methylamine (15.0 g). The mixture is stirred for 1 hr. and then allowed to stand for 18 hr. Water (100 ml) and ice chips are are added. After stirring for 15 min., the mixture is rendered alkaline with dilute NaOH solution and extracted with ether. The extract is washed with water, dried (MgSO$_4$) and concentrated to afford N-formyl-10,11-dihydro-5H-dibenzo[a,d]cycloheptene-10- methylamine, m.p. 109° - 111° C, $\delta_{max}^{CHCl_3}$ 3445, 3350, 1685 cm$^{-1}$, after recrystallization from ether.

EXAMPLE 335

N-Formyl-10,11-dihydro-5H-dibenzo[a,d]cycloheptene-10-methylamine (6.7 g, 0.027 mole), described in Example 334, in combined with polyphosphoric acid (50 g) and the mixture stirred for 3.5 hr. at 155° - 160° C. (bath temperature). The darkish reaction mixture is poured hot into stirred ice-water (400 ml). After stirring for 0.5 hr. (and treatment of the sticky precipitate with a glass rod) a solution of sodium hydroxide (60 g) in water is added, followed by chloroform. The chloroform solution is twice replaced by fresh chloroform and after 1 hr. the precipitate is almost dissolved. The combined chloroform solutions are washed with water, dried (Na$_2$SO$_4$) and taken to dryness to give a dark residue. The residue is dissolved in a little benzene and subjected to chromatography on neutral alumina (300 g). Elution with hexane-benzene (1:1) and benzene-ethyl acetate (9.5: 0.5) gives an oil which on crystallization from a concentrated ether solution gives 1,7,12,12a-tetrahydrobenzo[1,2]cyclohepta[4,5,6-de]isoquinoline, m.p. 91° - 93° C, $\gamma_{max}^{CHCl_3}$ 1629, 1588, 1578, 1490 cm$^{-1}$. The corresponding hydrochloride acid addition salt has m.p. 285° - 289° C, after recrystallization from chloroform-ether and methanol-ether.

EXAMPLE 336

By following the procedure of Example 171 but replacing 1,7,8,12b-tetrahydrobenzo[1,2]cyclohepta[3,4,5-de]isoquinoline hydrochloride with 1,7,12,12a-tetrahydrobenzo[1,2]cyclohepta[4,5,6-de]isoquinoline hydrochloride, described in Example 335, the aminoketone, 1,3,4,6,6a,10, 15,15a-octahydro-5H-benzo[5,6]cyclohepta[1,2,3-de]pyrido[2,1-a]isoquinolin-5-one is obtained as a mixture of isomers. The isomers are separated by subjecting the mixture to chromatography on silica gel. Continued elution with benzene-ethyl acetate (8.5: 1.5) gives first 1,3,4,6,6a,10,15,15a-octahydro-5H-benzo[5,6]cyclohepta[1,2,3-de]pyrido[2,1-a]isoquinolin-5-one (Isomer B), m.p. 192° - 194° C after recrystallization from benzene-hexane, and then 1,3,4,6,6a,10,15,15a-octahydro-5H-benzo[5,6]cyclohepta[1,2,3-de]pyrido[2,1-a]isoquinolin-5-one (Isomer A), m.p. 217° - 219° C after recrystallization from benzene.

The procedure of this example is used to prepare other aminoketones of which 1,3,4,6,6a,10,15,15a-octahydro-5H-benzo[5,6]cyclohepta[1,2,3-de]pyrido[2,1-a]isoquinolin-5-one is the parent aminoketone. In each case an equivalent amount of an appropriate unsaturated ketone of formula $$R^{12}R^{13}C=CR^{14}-\overset{O}{\underset{\|}{C}}-CHR^{15}R^{16},$$

in which R$^{12}$, R$^{13}$, R$^{14}$, R$^{15}$ and R$^{16}$ are as defined in the first instance, is used instead of 1-buten-3-one. Examples of such aminoketones are listed in Table XIII together with the appropriate unsaturated ketones used as starting materials.

TABLE XIII

| | STARTING MATERIAL $R^{12}R^{13}C=CR^{14}-\overset{O}{\underset{\|}{C}}-CHR^{15}R^{16}$ | | | | | AMINO KETONE PRODUCT: [(PREFIX LISTED BELOW)-1,3,4,-6,6a,10,15,15a-OCTAHYDRO-5H-BENZO[5,6]CYCLOHEPTA-[1,2,3-de]PYRIDO[2,1-a]- |
|---|---|---|---|---|---|---|
| EXAMPLE | R$^{12}$ | R$^{13}$ | R$^{14}$ | R$^{15}$ | R$^{16}$ | ISOQUINOLIN-5-ONE] |
| 337 | CH$_3$ | H | H | H | H | 3-methyl- |
| 338 | H | H | CH$_3$ | H | H | 4-methyl- |
| 339 | H | H | H | CH$_3$ | H | 6-methyl- |
| 340 | C$_2$H$_5$ | H | H | H | H | 3-ethyl- |
| 341 | H | H | C$_2$H$_5$ | H | H | 4-ethyl- |
| 342 | H | H | H | C$_2$H$_5$ | H | 6-ethyl- |
| 343 | n-C$_3$H$_7$ | H | H | H | H | 3-propyl- |
| 344 | H | H | n-C$_3$H$_7$ | H | H | 4-propyl- |
| 345 | H | H | H | n-C$_3$H$_7$ | H | 6-propyl- |
| 346 | CH$_3$ | CH$_3$ | H | H | H | 3,3-dimethyl- |
| 347 | H | H | H | CH$_3$ | CH$_3$ | 6,6-dimethyl- |
| 348 | H | H | H | C$_2$H$_5$ | C$_2$H$_5$ | 6,6-diethyl- |
| 349 | CH$_3$ | H | H | C$_2$H$_5$ | H | 6-ethyl-3-methyl- |
| 350 | CH$_3$ | CH$_3$ | H | H | n-C$_3$H$_7$ | 3,3-dimethyl-6-propyl- |
| 351 | CH$_3$ | CH$_3$ | CH$_3$ | CH$_3$ | CH$_3$ | 3,3,4,6,6-pentamethyl- |
| 352 | H | H | sec-C$_4$H$_7$ | H | H | 4-sec-butyl- |
| 353 | CH$_3$ | H | CH$_3$ | H | H | 3,4-dimethyl- |

EXAMPLE 354

To 50 ml of a solution of the lithium derivative, t-butyllithium, (1.8 M) in pentane, 1,3,4,6,6a,10,15,15a-octahydro-5H-benzo[5,6]cyclohepta[1,2,3-de]-pyrido[2,1-a]isoquinolin-5-one (Isomer A, 2.39 g, 7.9 mmoles), described in Example 336, dissolved in 150 ml of dry benzene is added dropwise with stirring and cooling. Cooling is continued for 4 hr. The reaction mixture is decomposed with 50 ml of 10% aqueous NH$_4$Cl solution and extracted with benzene. The benzene extract is washed with water, dried (MgSO$_4$) and concentrated to dryness. The residue is crystallized from chloroform-ether to give 5-t-butyl-1,4,5,6,6a,10,15,15a-octahydro-3H-benzo-[5,6]cyclohepta[1,2,3-de]pyrido[2,1-a]isoquinolin-5-ol (Isomer A), m.p. 180° - 182° C, $\gamma_{max}^{CHCl_3}$ 3620, 657 cm$^{-1}$, nmr (CDCl$_3$) δ0.96 (9H), 4.53 (1H), 7.09 (7H). The corresponding hydrochloric acid addition salt of this compound has m.p. 279° - 280° C after recrystallization from methanol-ether.

In the same manner but using the B isomer instead of the A isomer of 1,3,4,6,6a,10,15,15a-octahydro-5H-benzo[5,6]cyclohepta[1,2,3-de]pyrido[2,1-a]isoquinolin-5-one, described in Example 336, the B isomer of the product is obtained. In this case the crude residue from the extract of the reaction mixture is subjected to chromatography on neutral alumina. Elution with benzene and benzene-ethyl acetate (9:1) yields 5-t-butyl-1,4,5,6,6a,10,15,15a-octahydro-3H-benzo[5,6]cyclohepta[1,2,3-de]pyrido[2,1-a]isoquinolin-5-ol (Isomer B) $\gamma_{max}^{CHCl_3}$ 3610, 3360, 2970, 1462, 1138 cm$^{-1}$.

By following the procedure of this example, see also Examples 189 and 190, and using the appropriate aminoketone, for example, those described in Examples 336 to 353, together with the appropriate lithium derivative or Grignard reagent, then other 5-substituted derivatives of 1,4,5,6,6a,10,15,15a-octahydro-3H-benzo[5,6]-cyclohepta[1,2,3-de]pyrido[2,1-a]isoquinolin-5-ol, for example, the corresponding benzocycloheptaisoquinolines of formula Ia which correspond to the products listed in Tables VIII, IX, and X, are obtained. More specifically exemplified, 1,3,4,6,6a,10,15,15a-octahydro-5H-benzo[5,6]cyclohepta[1,2,3-de]pyrido[2,1-a]isoquinolin-5-one (Isomer A) (see Example 336) and isopropyl magnesium iodide give 5-isopropyl-1,4,5,6,6a,10,15,15a-octahydro-3H-benzo[5,6]cyclohepta[1,2,3-de]pyrido[2,1-a]isoquinolin-5-ol (Isomer A), $\gamma_{max}^{CHCl_3}$ 3614, 2970 cm$^{-1}$, and 3,3-dimethyl-1,3,4,6,6a,10,15,15a-octahydro-5H-benzo[5,6]cyclohepta[1,2,3-de]pyrido[2,1-a]isoquinolin-5-one (see Example 346) and ethyllithium give 3,3-dimethyl-5-ethyl-1,4,5,6,6a,10,15,15a-octahydro-3H-benzo[5,6]cyclohepta[1,2,3-de]pyrido[2,1-a]isoquinolin-5-ol. Likewise, 1,3,4,6,6a,10,15,15a-octahydro-5H-benzo[5,6]cyclohepta[1,2,3-de]pyrido[2,1-a]isoquinolin-5-one (Isomer A) (see Example 336) and ethyl magnesium bromide give 5-ethyl-1,4,5,6,6a,10,15,15a-octahydro-3H-benzo[5,6]-cyclohepta[1,2,3-de]pyrido[2,1-a]isoquinolin-5-ol (Isomer A), $\gamma_{max}^{CHCl_3}$ 3610, 2972 cm$^{-1}$.

We claim:

1. A compound selected from those of the formulae

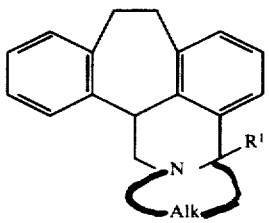

I and

Ia.

in which R$^1$ is selected from the group which consists of hydrogen and lower alkyl containing from 1-6 carbon atoms in a straight chain and up to 4 carbon atoms in a branched chain, and Alk represents

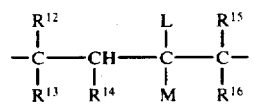

in which R$^{12}$, R$^{13}$, R$^{14}$, R$^{15}$ and R$^{16}$ are each the same or different radicals selected from the group which consists of hydrogen and lower alkyl containing from 1-6 carbon atoms in a straight chain and up to 4 carbon atoms in a branched chain, with the proviso that the carbon atom to which R$^{12}$ and R$^{13}$ are attached is bonded to the nitrogen atom of said compound; L represents hydroxyl or lower alkanoyloxy containing from 2-10 carbon atoms in a straight chain or from 4-6 carbon atoms in a branched chain; and M is selected from the group which consists of hydrogen, lower alkyl, lower alkenyl, lower alkynyl, cycloalkyl containing from three to six carbon atoms or cycloalkyl substituted with lower alkyl; phenyl or phenyl substituted with lower alkyl, lower alkoxy, halo, or trihalomethyl; benzyl, furyl, thienyl, or pyridyl; and their acid addition salts with pharmaceutically acceptable acids.

2. As claimed in claim 1, the compounds in which R$^1$ is hydrogen.

3. 1,4,5,6,6a,10,11,15b-Octahydro-3H-benzo[6,7]cyclohepta[1,2,3-de]pyrido[2,1-a]isoquinolin-5-ol, as claimed in claim 2.

4. 5-Acetoxy-1,4,5,6,6a,10,11,15b-octahydro-3H-benzo[6,7]cyclohepta[1,2,3-de]pyrido[2,1-a]isoquinoline, as claimed in claim 2.

5. 5-Ethyl-1,4,5,6,6a,10,11,15b-octahydro-3H-benzo[6,7]cyclohepta[1,2,3-de]pyrido[2,1-a]isoquinolin-5-ol, as claimed in claim 2.

6. 5-Butyl-1,4,5,6,6a,10,11,15b-octahydro-3H-benzo[6,7]cyclohepta[1,2,3-de]pyrido[2,1-a]isoquinolin-5-ol, as claimed in claim 2.

7. 5-Allyl-1,4,5,6,6a,10,11,15b-octahydro-3H-benzo[6,7]cyclohepta[1,2,3-de]pyrido[2,1-a]isoquinolin-5-ol, as claimed in claim 2.

8. 5-Isopropyl-1,4,5,6,6a,10,11,15b-octahydro-3H-benzo[6,7]cyclohepta[1,2,3-de]pyrido[2,1-a]isoquinolin-5-ol, as claimed in claim 2.

9. 5-Methyl-1,4,5,6,6a,10,11,15b-octahydro-3H-benzo[6,7]cyclohepta[1,2,3-de]pyrido[2,1-a]isoquinolin-5-ol, as claimed in claim 2.

10. 5-Cyclopropyl-1,4,5,6,6a,10,11,15b-octahydro-3H-benzo[6,7]cyclohepta[1,2,3-de]pyrido[2,1-a]isoquinolin-5-ol, as claimed in claim 2.

11. 5-Propyl-1,4,5,6,6a,10,11,15b-octahydro-3H-benzo[6,7]cyclohepta[1,2,3-de]pyrido[2,1-a]isoquinolin-5-ol, as claimed in claim 2.

12. 5-Hexyl-1,4,5,6,6a,10,11,15b-octahydro-3H-benzo[6,7]cyclohepta[1,2,3-de]pyrido[2,1-a]isoquinolin-5-ol, as claimed in claim 2.

13. 5-Phenyl-1,4,5,6,6a,10,11,15b-octahydro-3H-benzo[6,7]cyclohepta[1,2,3-de]pyrido[2,1-a]isoquinolin-5-ol, as claimed in claim 2.

14. 5-Cyclohexyl-1,4,5,6,6a,10,11,15b-octahydro-3H-benzo[6,7]cyclohepta[1,2,3-de]pyrido[2,1-a]isoquinolin-5-ol, as claimed in claim 2.

15. 5-t-Butyl-1,4,5,6,6a,10,11,15b-octahydro-3H-benzo[6,7]cyclohepta[1,2,3-de]pyrido[2,1-a]isoquinolin-5-ol, as claimed in claim 2.

16. 5-Ethynyl-1,4,5,6,6a,10,11,15b-octahydro-3H-benzo[6,7]cyclohepta[1,2,3-de]pyrido[2,1-a]isoquinolin-5-ol, as claimed in claim 2.

17. 5-Ethyl-1,4,5,6,6a,10,11,15b-octahydro-3H-benzo[6,7]cyclohepta[1,2,3-de]pyrido[2,1-a]isoquinolin-5-ol acetate, as claimed in claim 2.

18. 5-t-Butyl-1,4,5,6,6a,10,11,15b-octahydro-3H-benzo[6,7]cyclohepta[1,2,3-de]pyrido[2,1-a]isoquinolin-5-ol acetate, as claimed in claim 2.

19. 5-Ethyl-1,4,5,6,6a,10,11,15b-octahydro-3H-benzo[6,7]cyclohepta [1,2,3-de]pyrido[2,1-a]isoquinolin-5-ol heptanoate, as claimed in claim 2.

20. 3,3-Dimethyl-5-ethyl-1,4,5,6,6a,10,11,15b-octahydro-3H-benzo[6,7]cyclohepta[1,2,3-de]pyrido[2,1a]-isoquinolin-5-ol, as claimed in claim 2.

21. 3,4-Dimethyl-5-ethyl-1,4,5,6,6a,10,11,15b-octahydro-3H-benzo [6,7]cyclohepta[1,2,3-de]pyrido[2,1-a]isoquinolin-5-ol, as claimed in claim 2.

22. 5-Ethyl-6-methyl-1,4,5,6,6a,10,11,15b-octahydro-3H-benzo [6,7]cyclohepta[1,2,3-de]pyrido[2,1-a]isoquinolin-5-ol, as claimed in claim 2.

23. 4-sec-Butyl-5-isopropyl-1,4,5,6,6a,10,11,15b-octahydro-3H-benzo [6,7]cyclohepta[1,2,3,-de]-pyrido[2,1-a]isoquinolin-5-ol, as claimed in claim 2.

24. 4-sec-Butyl-1,4,5,6,6a,10,11,15b-octahydro-3H-benzo[6,7]cyclohepta [1,2,3,-de]pyrido[2,1-a]isoquinolin-5-ol, as claimed in claim 1.

25. 5-t-Butyl-1,4,5,6,6a,10,15,15a-octahydro-3H-benzo[5,6]cyclohepta[1,2,3-de]pyrido[2,1-a]isoquinolin-5-ol, as claimed in claim 2.

26. 5-Isopropyl-1,4,5,6,6a,10,15,15a-octahydro-3H-benzo [5,6]cyclohepta[1,2,3-de]pyrido[2,1-a]isoquinolin-5-ol, as claimed in claim 2.

27. 5-Ethyl-1,4,5,6,6a,10,15,15a-octahydro-3H-benzo[5,6]cyclohepta[1,2,3-de]pyrido[2,1-a]isoquinolin-5-ol, as claimed in claim 2.

28. A compound of the formula Ib

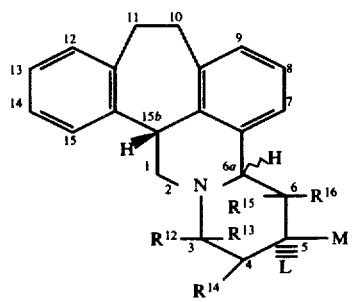

Ib in which $R^{12}$, $R^{13}$, $R^{14}$, $R^{15}$ and $R^{16}$ are each the same or different radicals selected from the group which consists of hydrogen and lower alkyl; L represents hydroxyl or lower alkanoyloxy containing from 2–10 carbon atoms in a straight chain or from 4–6 carbon atoms in a branched chain; and M is selected from the group which consists of lower alkyl, lower alkenyl, lower alkynyl, cycloalkyl containing 3–6 carbon atoms or cycloalkyl substituted with lower alkyl; phenyl or phenyl substituted with lower alkyl, lower alkoxy, halo, or trihalomethyl; benzyl, furyl, thienyl, or pyridyl; with the proviso that the hydroxyl or lower alkanoyloxy group is trans to the hydrogen atom in position 15b; and their acid addition salts with pharmaceutically acceptable acids.

29. (±), (5-OH, 15b-H-trans)-5-Ethyl-1,4,5,6,6a,10,11,15b-octahydro-3H-benzo-[6,7]cyclohepta[1,2,3-de]pyrido[2,1-a]isoquinolin-5-ol, as claimed in claim 28.

30. (±), (5-OH, 15b-H-trans)- 5-Butyl-1,4,5,6,6a,10,11,15b-octahydro-3H-benzo[6,7]cyclohepta [1,2,3-de]pyrido[2,1-a]isoquinolin-5-ol, as claimed in claim 28.

31. (±), (5-OH, 15b-H-trans)-5-Allyl-1,4,5,6,6a,10,11,15b-octahydro-3H-benzo[6,7]cyclohepta[1,2,3-de]pyrido[2,1-a]isoquinolin-5-ol, as claimed in claim 28.

32. (±), (5-OH, 15b-H-trans) 5-Isopropyl-1,4,5,6,6a,10,11,15b-octahydro-3H-benzo[6,7]cyclohepta[1,2,3-de]pyrido[2,1-a]isoquinolin-5-ol, as claimed in claim 28.

33. (+), (5-OH, 15b-H-trans) 5-Isopropyl-1,4,5,6,6a,10,11,15b-octahydro-3H-benzo[6,7]cyclohepta[1,2,3,-de]pyrido[2,1-a]isoquinolin-5-ol, as claimed in claim 28.

34. (±), (5-OH, 15b-H-trans) 5-Methyl-1,4,5,6,6a,10,11,15b-octahydro-3H-benzo[6,7]cyclohepta[1,2,3-de]pyrido[2,1-a]isoquinolin-5-ol, as claimed in claim 28.

35. (±), (5-CH, 15b-H-trans) 5-Cyclopropyl-1,4,5,6,6a,10,11,15b-octahydro-3H-benzo[6,7]cyclohepta[1,2,3-de]pyrido[2,1-a]isoquinolin-5-ol, as claimed in claim 28.

36. (±), (5OH, 15b-H-trans) -5-Propyl-1,4,5,6,6a,10,11,15b-octahydro-3H-benzo[6,7]cyclohepta[1,2,3-de]pyrido[2,1-isoquinolin-5-ol, as claimed in claim 28.

37. (±), (5-OH, 15b-H-trans) -5-Hexyl-1,4,5,6,6a,10,11,15b-octahydro-3H-benzo[6,7]cyclohepta[1,2,3-de]pyrido[2,1-a]isoquinolin-5-ol, as claimed in claim 28.

38. (±), (5-OH), (15b-H-trans) -5-Phenyl-1,4,5,6,6a,10,11,15b-octahydro-3H-benzo[6,7]cyclohepta[1,2,3-de]pyrido[2,1-a]isoquinolin-5-ol, as claimed in claim 28.

39. (+), (5-OH, 15b-H-trans) -5-Phenyl-1,4,5,6,6a,10,11,15b-octahydro-3H-benzo[6,7]cyclohepta[1,2,3-de]pyrido[2,1-a]isoquinolin-5-ol, as claimed in claim 28.

40. (±), (5-OH, 15b-H-trans) -5-Cyclohexyl-1,4,5,6,6a,10,11,15b-octahydro-3H-benzo[6,7]cyclohepta[1,2,3-de]pyrido[2,1-a]isoquinolin-5-ol, as claimed in claim 28.

41. (+), (5-OH, 15b-H-trans) -5-Cyclohexyl-1,4,5,6,6a,10,11,15b-octahydro-3H-benzo[6,7]cyclohepta[1,2,3,-de]pyrido[2,1-a]isoquinolin-5-ol, as claimed in claim 28.

42. (±), (5-OH, 15b-H-trans) -5-t-Butyl-1,4,5,6,6a,10,11,15b-octahydro-3H-benzo[6,7]cyclohepta[1,2,3-de]pyrido[2,1-a]isoquinolin-5-ol, as claimed in claim 28.

43. (±), (15b-H-trans) -5-t-Butyl-1,4,5,6,6a,10,11,15b-octahydro-3H-benzo[6,7]cyclohepta[1,2,3-de]-pyrido[2,1-a]isoquinolin-5-ol, as claimed in claim 28.

44. (±), (15b-H-trans) -5-Ethyl-1,4,5,6,6a,10,11,15b-octahydro-3H-benzo[6,7]cyclohepta[1,2,3-de]-pyrido[2,1-a]isoquinolin-5-ol acetate, as claimed in claim 28.

45. (±), (5-OH, 15b-H-trans) -5-t-Butyl-1,4,5,6,6a,10,11,15b-octahydro-3H-benzo[6,7]cyclohepta[1,2,3-de]pyrido[2,1-a]isoquinolin-5-ol acetate, as claimed in claim 28.

46. (±), (5-OH, 15b-H-trans) -5-Ethyl-1,4,5,6,6a,10,11,15b-octahydro-3H-benzo[6,7]cyclohepta[1,2,3-de]pyrido[2,1-a]isoquinolin-5-ol heptanoate, as claimed claim 28.

47. (±), (5-OH, 15b-H-trans) -3,3-Dimethyl-5-ethyl-1,4,5,6,6a,10,11,15b-octahydro-3H-benzo [6,7]cyclohepta[1,2,3-de]pyrido[2,1-a]isoquinolin-5-ol, as claimed in claim 28.

48. (±), (5-OH, 15b-H-trans) -3,4-Dimethyl-5-ethyl-1,4,5,6,6a,10,11,15b-octahydro-3H-benzo [6,7]cyclohepta[1,2,3-de]pyrido[2,1-a]isoquinolin-5-ol, as claimed in claim 28.

49. (±), (5-CH, 15b-H-trans) -5-Ethyl-6-methyl-1,4,5,6,6a,10,11,15b-octahydro-3H-benzo [6,7]cyclohepta[1,2,3-de]pyrido[2,1-a]isoquinolin-5-ol, as claimed in claim 28.

50. (±), (5-OH, 15b-H-trans) -4-sec-Butyl-5-isopropyl-1,4,5,6,6a,10,11,15b-octahydro-3H-benzo [6,7]cyclohepta[1,2,3-de]pyrido[2,1-a]isoquinolin-5-ol, as claimed in claim 28.

51. (±), (5-OH, 15b-H-trans)-4-sec-Butyl-1,4,5,6,6a,10,11,15b-octahydro-3H-benzo[6,7]cyclohepta[1,2,3-de]pyrido[2,1-a]isoquinolin-5-ol, as claimed in claim 28.

52. (±), (5-OH, 15b-H-trans)-4-sec-butyl-5-isopropyl-1,4,5,6,6a, 10,11,15b-octahydro-3H-benzo[6,7]cyclohepta[1,2,3-de]pyrido[2,1-a]isoquinolin- 5-ol, as claimed in claim 28.

53. (±), (5-OH, 15b-H-trans)-5-(3,4-dimethoxyphenyl)-1,4,5,6,6a,10,11,15b-octahydro-3H-benzo[6,7]-cyclohepta[1,2,3-de]pyrido [2,1-a]isoquinolin-5-ol, as claimed in claim 28.

54. (±), (5-OH,15b-H-trans)-5-o-anisyl-1,4,5,6,6a,10,11,15b-octahydro-3H-benzo[6,7]cyclohepta[1,2,3-de]pyrido [2,1-a]isoquinolin-5-ol, as claimed in claim 28.

55. (±), (5-OH, 15b-H-trans)-5m-fluorophenyl-1,4,5,6,6a,10,11,15b-octahydro-3H-benzo[6,7]cyclohepta[1,2,3de]pyrido [2,1-a]isoquinolin-5-ol, as claimed in claim 28.

56. (±), (5-OH, 15b-H-trans)-5-o-chlorophenyl-1,4,5,6,6a,10,11,15b-octahydro-3H-benzo[6,7]cyclohepta[1,2,3-de]pyrido[2,1-a]isoquinolin-5ol, as claimed in claim 28.

57. (±), (5-OH, 15b-H-trans)-5-p-bromophenyl-1,4,5,6,6a,10,11,15b-octahydro-3H-benzo[6,7]cyclohepta[1,2,3-de]pyrido[2,1-a]isoquinolin-5-ol, as claimed in claim 28.

58. (±), (5-OH, 15b-H-trans)-5-o-trifluoromethylphenyl-1,4,5,6,6a,10,11,15b-octahydro-3H-benzo[6,7]cyclohepta[1,2,3-de]pyrido[2,1-a]isoquinolin-5-ol, as claimed in claim 28.

59. (±), (5-OH, 15b-H-trans)-5-o-tolyl-1,4,5,6,6a,10,11,15b-octahydro-3H-benzo[6,7]cyclohepta[1,2,3-de]pyrido[2,1-a]isoquinolin-5-ol, as claimed in claim 28.

60. (±), (5-OH, 15b-H-trans)-5-m-anisyl-1,4,5,6,6a,10,11,15b-octahydro-3H-benzo[6,7]cyclohepta[1,2,3-de]pyrido[2,1-a]isoquinolin-5ol, as claimed in claim 28.

61. (±), (5-OH, 15b-H-trans)-5-p-anisyl-1,4,5,6,6a,10,11,15b-octahydro-3H-benzo[6,7]cyclohepta [1,2,3-de]pyrido [2,1-a]isoquinolin-5-ol, as claimed in claim 28.

62. (±), (5-OH, 15b-H-trans)-5-(2-thienyl)-1,4,5,6,6a,10,11,15b-octahydro-3H-benzo[6,7]cyclohepta[1,2,3-de]pyrido [2,1-a]isoquinolin-5-ol, as claimed in claim 28.

63. (±), (5-OH, 15b-H-trans)-5-(3-thienyl)-1,4,5,6,6a,10,11,15b-octahydro-3H-benzo[6,7]cyclohepta[1,2,3-de]pyrido [2,1-a]isoquinolin-5-ol, as claimed in claim 28.

64. (±), (5-OH, 15b-H-trans)-5-(2-furyl)-1,4,5,6,6a,10,11,15b-octahydro-3H-benzo[6,7]cyclohepta[1,2,3-de]pyrido [2,1-a]isoquinolin-5-ol, as claimed in claim 28.

65. (±), (5-OH, 15b-H-trans)-5-benzyl-1,4,5,6,6a,10,11,15b-octahydro-3H-benzo[6,7]cyclohepta[1,2,3-de]pyrido [2,1-a]isoquinolin-5-ol, as claimed in claim 28.

66. (±), (5-OH, 15b-H-trans)-5-(3-pyridyl)-1,4,5,6,6a,10,11,15b-octahydro-3H-benzo[6,7]cyclohepta[1,2,3-de]pyrido [2,1-a]isoquinolin-5ol, as claimed in claim 28.

* * * * *